(12) United States Patent
Ziegler et al.

(10) Patent No.: US 7,083,952 B2
(45) Date of Patent: Aug. 1, 2006

(54) NUCLEOTIDE SEQUENCES CODING FOR PROTEINS INVOLVED IN THE BIOSYNTHESIS OF L-SERINE, AN IMPROVED METHOD FOR THE MICROBIAL PRODUCTION OF L-SERINE AND A GENETICALLY MODIFIED MICROORGANISM SUITABLE THEREFOR

(75) Inventors: Petra Ziegler, Cambridge (GB); Lothar Eggeling, Jülich (DE); Hermann Sahm, Jülich (DE); Petra Peters-Wendisch, Jülich (DE)

(73) Assignee: Forschungszentrum Jülich GmbH, Jülich (DE)

( * ) Notice: Subject to any disclaimer, the term of this patent is extended or adjusted under 35 U.S.C. 154(b) by 0 days.

(21) Appl. No.: 10/224,574

(22) Filed: Aug. 21, 2002

(65) Prior Publication Data

US 2004/0101837 A1     May 27, 2004

Related U.S. Application Data

(63) Continuation-in-part of application No. PCT/EP01/02283, filed on Mar. 1, 2001.

(30) Foreign Application Priority Data

Mar. 1, 2000 (DE) ............................. 100 09 799
Sep. 11, 2000 (DE) ............................. 100 44 831

(51) Int. Cl.
| | |
|---|---|
| C12P 13/06 | (2006.01) |
| C12N 1/20 | (2006.01) |
| C12N 15/00 | (2006.01) |
| C12N 5/00 | (2006.01) |
| C12N 9/10 | (2006.01) |
| C12N 9/12 | (2006.01) |
| C12P 21/06 | (2006.01) |
| C07H 21/04 | (2006.01) |

(52) U.S. Cl. ............... 435/116; 435/252.32; 435/16; 435/21; 435/69.1; 435/471; 435/193; 435/196; 435/320.1; 435/252.3; 435/325; 536/23.2

(58) Field of Classification Search .................. 435/16, 435/21, 116, 69.1, 471, 193, 196, 320.1, 252.3, 435/325, 252.32; 536/23.2
See application file for complete search history.

(56) References Cited

U.S. PATENT DOCUMENTS 5,380,657 A    1/1995 Schaefer et al.

FOREIGN PATENT DOCUMENTS

| EP | 0 931 833 A | 7/1999 |
|---|---|---|
| EP | 1 108 790 A | 6/2001 |
| WO | WO 01 00843 A | 1/2001 |
| WO | WO 2001/00843 | * 4/2001 |

OTHER PUBLICATIONS

Witkowski et al., Biochemistry 38:11643-11650, 1999.*
Seffernick et al., J. Bacteriol. 183(8):2405-2410, 2001.*
Simic et al., J. Bacteriol. 183(18):5317-5324, 2001.*
Berger S and Kimmel A: Methods in enzymology, vol. 152, 1988, Academic press, San Diego, pp. 516-517.
Database WPI; section Ch, week 199249, Derwent Publications Ltd., London, GB; AN 1992-405386; & SU 1 412 288 A (Ind Microorganisms Genetics Selection)Dec. 7, 1991 Summary.
Database WPI; Section Ch, Week 199431; Derwent Publications Ltd. London, GB; AN1994-251695; JP 06 181776 A (Kyowa Hakko Kogyo KK); Jul. 5, 1994; Summary.
Lehninger A: "Biochemistry" 1972, Worth Publishers Inc, New York, pp. 539-555.

* cited by examiner

*Primary Examiner*—Rebecca Prouty
*Assistant Examiner*—Delia M. Ramirez
(74) *Attorney, Agent, or Firm*—Klaus J. Bach

(57) ABSTRACT

The present invention relates to nucleotide sequences of coryneform bacteria, coding for proteins involved in the bio-synthesis of L-serine and to methods for the isolation thereof. The invention further relates to an improved method for the production of L-serine. In addition, the present invention relates to the use of L-serine in the food, animal feed and/or pharmaceutical industries or in human medicine.

2 Claims, 3 Drawing Sheets

Figure 1:
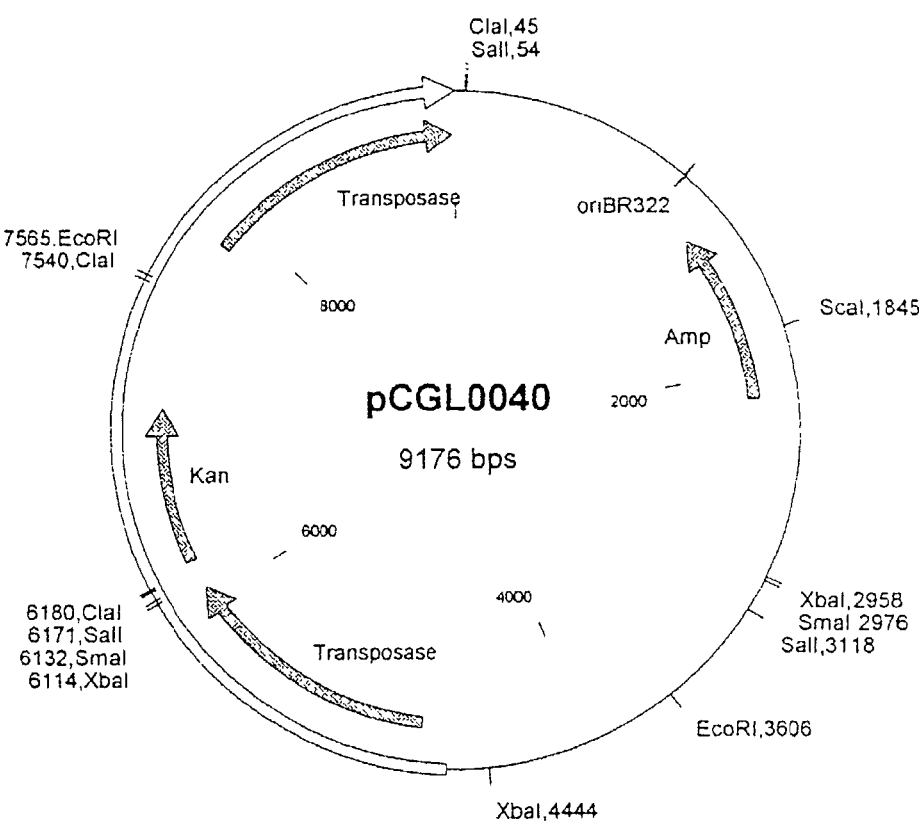

NUCLEOTIDE SEQUENCES CODING FOR PROTEINS INVOLVED IN THE BIOSYNTHESIS OF L-SERINE, AN IMPROVED METHOD FOR THE MICROBIAL PRODUCTION OF L-SERINE AND A GENETICALLY MODIFIED MICROORGANISM SUITABLE THEREFOR

This is a c-i-p application of international application PCT/EP01/02283 filed Mar. 1, 2001 and claiming the priority of German applications 100 09 799.5 filed Mar. 1, 2000 AND 100 44 831 3 filed Sep. 11, 2000.

BACKGROUND OF THE INVENTION

The present invention relates to nucleotide sequences of coryneform bacteria, coding for proteins involved in the bio-synthesis of L-serine and to an improved method for the microbial production of L-serine and to a genetically modified microorganism suitable therefor. The present invention further comprises the use of L-serine and/or secondary products thereof in the food, animal feed and/or pharmaceutical industries and/or in human medicine.

In recent years, amino acids such as L-glutamate, L-lysine or branched-chain L-amino acids have increasingly become the focus of economic interest. This is equally true for the amino acid L-serine which serves not only as a precursor for the synthesis of the aliphatic amino acids L-glycine or L-cysteine but also for the production of L-tryptophan from indole and L-serine. To this end, the amino acid L-serine is regarded to have an increasingly economic potential, in particular in the food, animal feed and pharmaceutical industries and also in many areas of human medicine.

Numerous methods for the microbial production of L-serine have been described in the literature. In addition, fermentations of coryneform bacteria for the production of L-serine are already known. Thus, for example, a *Corynebacterium glyciniphilum* strain is capable of forming L-serine from glycine and carbohydrates (Kubota K., Kageyama K., Shiro T., and Okumura S., (1971), Journal of General Applications in Microbiology, 17: 167–168; Kubota K., Kageyama K., Maeyashiki I., Yamada K., and Okumura S., (1972), Journal of General Applications in Microbiology 18: 365). Here, the enzyme L-serine hydroxymethyltransferase is involved in converting glycine to L-serine (Kubota K. and Yokozeki K., (1989), Journal of Fermentation and Bioengineering, 67(6): 387–390). Furthermore, the bacterial strains used exhibit a reduced serine degradation which can be attributed to a reduction in the activity of the enzyme L-serine dehydratase (Kubota K., Kageyama K., Shiro T. and Okumura S., (1971) Journal of General Applications in Microbiology, 17: 167–168; Kubota K., (1985), Agricultural Biological Chemistry, 49: 7–12).

Furthermore, the fermentative production of L-serine from methanol and glycine with the aid of methylotrophic bacteria, for example of the genus *Hyphomicrobium*, is described in Izumi Y., Yoshida T., Miyazaki S. S., Mitsunaga T., Ohshiro T., Shiamo M., Miyata A. and Tanabe T., (1993), Applied Microbiology and Biotechnology, 39: 427–432.

In the aforementioned cases, however, formation of the amino acid L-serine starting from carbohydrates requires the addition of the amino acid glycine as a precursor.

Furthermore, methods for fermentation of coryneform bacteria which are capable of producing L-serine directly from carbohydrates without addition of further precursors are already known. Thus, for example, Yoshida H. and Nakayama K., (1974), Nihon-Nogei-Kagakukaishi 48: 201–208 describe bacterial strains of the genus *Corynebacterium* and, in particular, of the species *Corynebacterium glutamicum*, which have been obtained by random mutagenesis and which are distinguished, inter alia, by a resistance to the L-serine analogs serine hydroxamate and β-chloroalanine. This causes, inter alia, the metabolic flow to be able to flow increasingly in the direction of L-serine biosynthesis, since the activity of the corresponding enzymes is less inhibited by the final product.

EP 0 931 833 discloses bacterial strains of the species *Brevibacterium flavum* which were likewise obtained by random mutagenesis and which therefore have defective serine degradation. In addition, the strains described there have a modified serA gene which codes for a feedback-insensitive 3-phosphoglycerate dehydrogenase. These strains additionally contain the genes serB and serC which originate from the heterologous organism *Escherichia coli* and which code for the enzymes phosphoserine phosphatase and phosphoserine aminotransferase, respectively. The system described here thus has a high complexity with respect to the multiplicity of additionally introduced, partially heterologous, gene structures, combined with a genetic uncertainty of the bacterial strains with respect to the initially mentioned random mutagenesis. This holds the risk of a relatively high instability of such bacterial strains during the course of a large-scale production process. It has further been described that the bacterial strains illustrated here only achieve an increase in L-serine production by a factor of 2 to 5, at most. The reason for this may be, inter alia, a suboptimal expression of heterologous genes.

Another disadvantage of heterologous systems is the low acceptance of foreign DNA-containing systems, in particular for the production of medically and pharmacologically relevant substances and of substances relevant to food.

Besides the biosynthesis of economically interesting L-amino acids such as, for example, L-serine, secretion of these metabolic products into the culture medium is also crucially important for the yield of L-serine in the final product. This export may be unspecific due to diffusion or actively mediated by membrane transport systems, as described, for example, for the amino acids L-isoleucine or L-lysine (Zittrich S. et al., 1994, Journal of Bacteriology, 176: 6892–6899 and Broer S. et al., 1991, European Journal of Biochemistry, 202: 131–153). A problem of those active transport systems is that the capacity of these "export carriers" is quickly exceeded, as soon as the contents of the metabolic product to be transported in the cell exceeds a threshold of the naturally present concentration. This means that, for example in the case of an increased biosynthesis of L-serine, the export thereof out of the cell may be limited.

Consequently, the availability of the genes from coryneform bacteria, which are crucially involved in the biosynthesis of L-serine, for expression in a homologous system is desirable, as is an improved secretion of the L-serine formed into the culture medium.

It is therefore an object of the present invention to provide a system which no longer has the aforementioned disadvantages and makes possible an improved production of L-serine or of metabolic products derivable therefrom and the isolation thereof.

SUMMARY OF THE INVENTION

The present invention relates to nucleotide sequences of coryneform bacteria, coding for proteins involved in the biosynthesis of L-serine and to methods for the isolation thereof. The invention further relates to an improved method for the production of L-serine. In addition, the present invention relates to the use of L-serine in the food, animal feed and/or pharmaceutical industries or in human medicine.

More specifically, the invention relates to providing an isolated nucleic acid which codes for a phosphoserine phosphatase and which comprises a gene serB selected from the sequences according to the SEQ ID No. 1 or 5 and 2 or 6 (FIG. 1) and an isolated nucleic acid which codes for a phosphoserine aminotransferase and which comprises a gene serC selected from the sequences according to the SEQ ID No. 3 or 7 and 4 or 8 (FIG. 1) or an allele, homolog or derivative of these nucleotide sequences or nucleotide sequences hybridizing to these nucleotide sequences.

The present invention likewise includes the nucleic acids coding for an L-threonine export carrier according to SEQ ID No. 9 or 11 and the polypeptide sequences according to SEQ ID No. 10 or 12 derived therefrom and also the use thereof in the inventive methods for the production of L-serine. The German patent application 199 41 478.5 discloses the isolation of said sequences from coryneform bacteria.

The nucleic acids used are distinguished by the fact that they are isolated from coryneform bacteria, preferably of the genus *Corynebacterium* or *Brevibacterium*, particularly preferably of the species *Corynebacterium glutamicum* or *Brevibacterium flavum*. Examples of wild-type coryneform bacteria deposited in stock cultures are *Corynebacterium glutamicum* ATCC 13032, *Corynebacterium glutamicum* ATCC 14752, *Corynebacterium acetoglutamicum* ATCC 15806, *Corynebacterium acetoglutamicum* ATCC 15806, *Corynebacterium melassecola* ATCC 17965, *Corynebacterium thermoaminogenes* FERM BP-1539, *Brevibacterium flavum* ATCC 14067, *Brevibacterium lactofermentum* ATCC 13869 and *Brevibacterium divaricatum* ATCC 14020. Examples of mutants or production strains suitable for the production of L-serine are *Corynebacterium glutamicum* ATCC 21586, *Corynebacterium glutamicum* KY 10150 and *Brevibacterium ketoglutamicum* ATCC 21222. The present invention is characterized in more detail by stating the aforementioned bacterial strains; this is not limiting, however.

According to the invention, an isolated nucleic acid or an isolated nucleic acid fragment means an RNA or DNA polymer which may be single- or double-stranded and which may contain natural, chemically synthesized, modified or artificial nucleotides. In this connection, the term DNA polymer also includes genomic DNA, cDNA or mixtures thereof.

In accordance with the invention, alleles mean functionally equivalent, i.e. essentially identically acting, nucleotide sequences. Functionally equivalent sequences are those sequences which, despite a deviating nucleotide sequence, still have the desired functions, for example due to the degeneracy of the genetic code. Functional equivalents thus comprise naturally occurring variants of the sequences described herein and also artificial nucleotide sequences which have been obtained, for example, by chemical synthesis and, where appropriate, have been adapted to the codon usage of the host organism. In addition, functionally equivalent sequences comprise those which have a modified nucleotide sequence which imparts to the enzyme, for example, an insensitivity or resistance to inhibitors.

A functional equivalent means in particular also natural or artificial mutations of an originally isolated sequence which continue to display the desired function. Mutations comprise substitutions, additions, deletions, exchanges or insertions of one or more nucleotide residues.

"Sense mutations" which can lead at the protein level, for example, to the exchange of conserved amino acids but which do not result in any fundamental change in the activity of the protein and are thus functionally neutral are also included here. This also includes modifications of the nucleotide sequence which, at the protein level, relate to the N- or C-terminus of a protein but which do not substantially impair the function of the protein. These modifications may even have a stabilizing influence on the structure of the protein.

Furthermore, the present invention also includes, for example, those nucleotide sequences which are obtained by modification of the nucleotide sequence, resulting in corresponding derivatives. The aim of such a modification may be, for example, a further narrowing-down of the coding sequence contained therein or else, for example, the introduction of further restriction enzyme cleavage sites. Functional equivalents are also those variants whose function is reduced or increased, compared with the starting gene or gene fragment.

Moreover, the present invention relates to artificial DNA sequences, as long as they provide for the desired properties, as described above. Such artificial DNA sequences may be determined, for example, by back-translating proteins which have been produced by means of computer programs (molecular modeling) or by in-vitro selection. Coding DNA sequences which have been obtained by back-translating a polypeptide sequence according to the host-specific codon usage are particularly suitable. The specific codon usage can be readily determined by a skilled worker familiar with molecular genetic methods by using computer analysis of other, already known genes of the organism to be transformed.

According to the invention, homologous sequences are to be considered those which are complementary to the nucleotide sequences of the invention and/or hybridized to these nucleotide sequences. The term hybridizing sequences includes according to the invention substantially similar nucleotide sequences of the group comprising DNA and RNA, which specifically interact with (bind to) the aforementioned nucleotide sequences under stringent conditions known per se. This also includes short nucleotide sequences of, for example, from 10 to 30, preferably 12 to 15, nucleotides in length. According to the invention, this also includes, inter alia, "primers" or "probes".

The invention also includes the sequence regions 5' upstream and/or the sequence regions 3' downstream of the coding regions (structural genes). This includes in particular sequence regions having a regulatory function. They can influence transcription, RNA stability or RNA processing and translation. Examples of regulatory sequences are, inter alia, promoters, enhancers, operators, terminators and translation enhancers.

The present invention further relates to a gene structure comprising at least one of the above-described nucleotide sequences coding for a phosphoserine phosphatase, a phosphoserine aminotransferase and/or an L-threonine export carrier and also to regulatory sequences operatively linked thereto, which control expression of the coding sequences in the host cell.

An operative linkage means the sequential arrangement of, for example, promoter, coding sequence, terminator and, where appropriate, further regulatory elements such that each of the regulatory elements can carry out properly its function during expression of the coding sequence. These regulatory nucleotide sequences may be of natural origin or obtained by chemical synthesis. A suitable promoter is in principle any promoter which is capable of controlling gene expression in the appropriate host organism. According to the invention, this promoter may also be a chemically inducible promoter which makes it possible to control expression of the genes controlled by said promoter in the host cell at a particular time. An example which may be mentioned here is a promoter inducible by IPTG (isopropyl-β-thiogalactoside) (Eikmanns, B. J. et al., 1991, Gene, 102: 93–98).

A gene structure is prepared by fusing a suitable promoter to at least one nucleotide sequence of the invention according to recombination and cloning techniques as are described, for example, in T. Maniatis, E. F. Fritsch and J. Sambrook, Molecular Cloning: A Laboratory Manual, Cold Spring Harbor Laboratory, Cold Spring Harbor, N.Y. (1989).

The DNA fragments may be linked to one another by attaching adapters or linkers to the fragments.

In addition, the present invention relates to a vector comprising at least one nucleotide sequence of the above-described type, coding for a phosphoserine phosphatase, a phosphoserine aminotransferase and/or an L-threonine export carrier, to regulatory nucleotide sequences operatively linked thereto and to additional nucleotide sequences for the selection of transformed host cells, for replication within the host cell or for integration into the corresponding host-cell genome. The vector of the invention may further comprise a gene structure of the abovementioned type.

Suitable vectors are those which are replicated in coryneform bacteria (Process Biochem 33 (1998) 147–161). Numerous known plasmid vectors such as, for example, pZ1 (Menkel et al., Applied and Environmental Microbiology (1989) 64: 549–554), pEKEx1 (Eikmanns et al., Gene 102: 93–98 (1991)) or pHS2-1 (Sonnen et al., Gene 107: 69–74 (1991)) are based on the cryptic plasmids pHM1519, pBL1 or pGA1. Other plasmid vectors such as, for example, those based on pCG4 (U.S. Pat. No. 4,489,160), or pNG2 (Serwold-Davis et al., FEMS Microbiology Letters 66, 119–124 (1990)), or pAG1 (U.S. Pat. No. 5,158,891), may be used in the same way. However, the present invention is not limited by this list.

It is possible, by utilizing the nucleic acid sequences according to the SEQ ID No. 1, 3, 5, 7, 9 or 11 to synthesize appropriate probes or else primers and to use them, for example with the aid of the PCR technique, to amplify and isolate analogous genes from other microorganisms, preferably coryneform bacteria.

The present invention therefore also relates to a probe for identifying and/or isolating genes coding for proteins involved in the biosynthesis of L-serine or in the export of L-threonine and/or L-serine, said probe being prepared starting from the nucleic acid sequences of the above-described type and containing a label suitable for detection. The probe may be a part section of the sequence of the invention, for example from a conserved region, which is, for example, from 10 to 30 or preferably 12 to 15 nucleotides in length and which can hybridize specifically to homologous nucleotide sequences under stringent conditions. Numerous suitable labels are known from the literature.

Relevant instructions can be found by the skilled worker, inter alia, in the manual by Gait: Oligonucleotide synthesis: a practical approach (IRL Press, Oxford, UK, 1984) and in Newton and Graham: PCR (Spektrum Akademischer Verlag, Heidelberg, Germany, 1994), for example, or in the manual "The DIG System Users Guide for Filter Hybridization" from Roche Diagnostics (Mannheim, Germany) and in Liebl et al., (International Journal of Systematic Bacteriology (1991) 41: 255–260), for example.

The present invention further relates to a phosphoserine phosphatase or a part thereof encoded by a nucleic acid sequence selected from the sequences according to the SEQ ID No. 1 or 5 or variations thereof of the above-described type. The present invention likewise comprises a phosphoserine phosphatase having an amino acid sequence selected from the sequences according to the SEQ ID No. 2 or 6 or a modified form of these polypeptide sequences or isoforms thereof or mixtures thereof.

The invention likewise comprises a phosphoserine aminotransferase or a part thereof encoded by a nucleic acid sequence selected from the sequences according to the SEQ ID No. 3 or 7 or variations thereof of the above-described type. The present invention likewise relates to a phosphoserine phosphatase having an amino acid sequence selected from the sequences according to the SEQ ID No. 4 or 8 or a modified form of these polypeptide sequences or isoforms thereof or mixtures thereof.

The present invention also includes the use of the L-threonine export carrier having an amino acid sequence selected from the sequences according to SEQ ID No. 10 or 12 or a modified form of these polypeptide sequences or isoforms thereof or mixtures thereof, said carrier also mediating L-serine transport and being encoded by a nucleic acid sequence selected from the sequences according to SEQ ID No. 9 or 11 or variations thereof.

The polypeptides of the invention are further distinguished by the fact that they originate from coryneform bacteria, preferably of the genus *Corynebacterium* or *Brevibacterium*, particularly preferably of the species *Corynebacterium glutamicum* or *Brevibacterium flavum*.

Isoforms mean enzymes which have identical or comparable substrate and action specificities but which have a different primary structure.

According to the invention, modified forms mean enzymes which contain changes in the sequence, for example at the N- and/or C-terminus of the polypeptide or in the region of conserved amino acids, but whose function is not impaired. These modifications may be carried out in the form of amino acid exchanges according to methods known per se.

A particular embodiment of the present invention comprises variants of the polypeptides of the invention, whose activity, compared to the particular starting protein, is reduced or increased, for example by amino acid exchanges. The same is true for the stability of the enzymes of the invention in the cells, which are, for example, susceptible to degradation by proteases in an increased or reduced manner.

The present invention further relates to polypeptides having the function of a phosphoserine phosphatase or phosphoserine aminotransferase, whose amino acid sequence has been modified such that they are insensitive to regulatory compounds, for example the final metabolic products regulating their activity (feedback insensitive).

The present invention further relates to the transfer of at least one of the nucleic acid sequences or a part thereof coding for a phosphoserine phosphatase or phosphoserine aminotransferase, an allele, homolog or derivative thereof according to SEQ ID No. 1, 3, 5 or 7 and of a nucleic acid sequence coding for an L-threonine export carrier, an allele, homolog or derivative thereof according to SEQ ID No. 9 or 11 into a homologous host system. This also includes the transfer of an above-described gene construct or vector into a homologous host system. This DNA transfer into a host cell is carried out using genetic engineering methods. A preferred method which may be mentioned here is transformation and, particularly preferably, the transfer of DNA by electroporation.

A homologous host system means microorganisms which all belong to a related family. According to the invention, this means coryneform bacteria into which the nucleic acids isolated from coryneform bacteria according to the invention are introduced. A transformed microorganism resulting from a successfully carried out nucleic acid transfer thus differs from the correspondingly untransformed microorganism by containing additional nucleic acids of the type of the invention and by being able to express them accordingly. A representative for a suitable homologous host system, which may be mentioned, is the bacterium *Corynebacterium glutamicum*, preferably the strain ATCC 13032, which can be cultured under standard conditions as follows:

Culturing is carried out in 500 ml shaker flasks at 120 rpm and 30° C., using 50 ml of culture medium per flask. The culture medium is inoculated by adding a bacterial (pre) culture of the strain *Corynebacterium glutamicum* ATCC 13032 which has been grown earlier under identical conditions over a period of 12–16 hours, the inoculated culture medium having an optical density in the range from 0.7 to 1.5.

Depending on the requirements, a suitable culture medium is a complex medium such as, for example, LB medium (T. Maniatis, E. F. Fritsch and J. Sambrook, Molecular Cloning: A Laboratory Manual, Cold Spring Harbor Laboratory, Cold Spring Harbor, N.Y. (1989)) or else a mineral salt medium such as, for example, CGXII medium (Keilhauer, C. et al., 1993, J. Bacteriol., 175: 5593–5603). After appropriate culturing, the bacterial suspension can be harvested and used for further studies, for example for transformation or isolation of nucleic acids according to common methods.

This procedure may also be applied in a similar way to other strains of coryneform bacteria. The preferred host systems are bacteria of the genus *Corynebacterium* or *Brevibacterium*. Within the genus *Corynebacterium*, particular preference is given to the species *Corynebacterium glutamicum*, and within the genus *Brevibacterium*, particular preference is given to the species *Brevibacterium flavum*. Representatives of these genera include on the one hand strains which have been characterized through their properties as wild type. Examples which may be mentioned here are *Corynebacterium glutamicum* ATCC 13032, *Corynebacterium glutamicum* ATCC 14752, *Corynebacterium acetoglutamicum* ATCC 15806, *Corynebacterium acetoglutamicum* ATCC 15806, *Corynebacterium melassecola* ATCC 17965, *Corynebacterium thermoaminogenes* FERM BP-1539, *Brevibacterium flavum* ATCC 14067, *Brevibacterium lactofermentum* ATCC 13869 and *Brevibacterium divaricatum* ATCC 14020.

In addition, the present invention also includes bacterial strains which are distinguished as L-serine-producing mutants or production strains. These may be prepared, for example starting from wild-type strains, by classical (chemical or physical) or genetic methods. Examples of strains suitable according to the invention are, inter alia, *Corynebacterium glutamicum* ATCC 21586, *Corynebacterium glutamicum* KY 10150 and *Brevibacterium ketoglutamicum* ATCC 21222. The selected examples of microorganisms characterize the present invention in more detail without limiting it.

The invention includes, besides the above-described bacterial strains which are distinguished as L-serine producers, also those production strains which have improved secretion of the desired metabolic products, preferably of L-amino acids, from the cells into the culture medium. This improved secretion may be achieved, for example, by overexpressing one or more genes coding for membrane transport proteins, for example export carrier proteins, inter alia specific L-amino-acid export carrier proteins.

In a particular embodiment of the present invention, the bacterial strain used for the production of L-serine is distinguished in that it is a genetically modified microorganism containing, in a replicable form, a nucleic acid coding for a phosphoserine phosphatase (serB) and/or a nucleic acid coding for a phosphoserine aminotransferase (serC) according to SEQ ID No. 1, 3, 5 or 7 and a nucleic acid coding for the L-threonine export carrier (thrE) according to SEQ ID No. 9 or 11, whose expression is enhanced and/or whose copy number is increased, compared to the correspondingly genetically unmodified microorganism.

The invention likewise comprises a genetically modified microorganism which contains polypeptides encoded by the genes serB and/or serC according to SEQ ID No. 2, 4, 6 or 8 and thrE according to SEQ ID No. 10 or 12, which have an increased activity and/or lifespan and/or a reduced final-product inhibition compared to the correspondingly genetically unmodified microorganism. Thus, the present invention likewise relates to a genetically modified microorganism which has at least an increased rate of production of L-serine and additionally an increased rate of secretion of L-serine and/or L-threonine.

The present invention likewise comprises a genetically modified microorganism containing, in a replicable form, a gene structure or a vector of the above-described type. A microorganism genetically modified according to the invention is further distinguished in that it is a coryneform bacterium, preferably of the genus *Corynebacterium* or *Brevibacterium*, particularly preferably of the species *Corynebacterium glutamicum* or *Brevibacterium flavum*.

In principle, it is possible to amplify genes by methods known per se, such as, for example, the polymerase chain reaction (PCR) with the aid of short synthetic nucleotide sequences (primers), and then isolate them. The primers used are prepared in general on the basis of known gene sequences, due to existing homologies in conserved regions of the genes, and/or by taking into account the GC content of the DNA of the microorganism to be studied. However, this method has a number of disadvantages which are, for example, due to the defectiveness of the PCR method itself or to the fact that the gene sequences to be identified are less homologous to the already known sequences than assumed. This may cause the primers used to bind unspecifically or even fail to bind to the nucleic acid sequence to be studied.

Another procedure for isolating coding nucleotide sequences is complementation of "defective" mutants of the organism to be studied, which have at least phenotypically a functionally reduced activity of the gene to be studied or of the corresponding protein. Complementation means the removal of the genetic defect of the mutant and substantial restoration of the original phenotype prior to mutagenesis, which is achieved by introducing functional genes or gene fragments from the microorganism to be studied.

An example of a classical mutagenesis method for producing defective mutants is the treatment of bacterial cells with chemicals such as, for example, N-methyl-N-nitro-N-nitrosoguanidine or UV radiation. Such methods for causing mutations are generally known and can be found, inter alia, in Miller (A Short Course in Bacterial Genetics, A Laboratory Manual and Handbook for *Escherichia coli* and Related Bacteria (Cold Spring Harbor Laboratory Press, 1992)) or in the "Manual of Methods for General Bacteriology" of the American Society for Bacteriology (Washington D.C., USA, 1981). Disadvantages here are a time-consuming and costly selection of mutants having the desired phenotype and the fact that the isolated mutants are genetically undefined, since the mutagenesis has been random. The latter frequently leads to unexpected problems, for example with respect to the stability of these mutants during a large-scale production process.

It is another object of the present invention to provide a method for isolating coding nucleic acid sequences from coryneform bacteria, which no longer has the disadvantages mentioned. The following description illustrates in more detail how the object is achieved according to the invention.

The invention relates to a method for isolating the nucleic acids of the invention, generating a coryneform bacterium whose genes serB and serC contain defects generated by transposon mutagenesis.

The method of transposon mutagenesis makes use of the property of a transposon which is capable of "jumping" into DNA sequences and thereby interfering with or eliminating the function of the gene in question.

Examples of transposons of coryneform bacteria are listed below. Thus the erythromycin-resistance transposon Tn5432 (Tauch et al., Plasmid (1995) 33: 168–179) and the chloroamphenicol-resistance transposon Tn5546 were isolated from the *Corynebacterium xerosis* strain M82B. Tauch et al. (Plasmid (1995) 34: 119–131 and Plasmid (1998) 40: 126–139) showed that it is possible to carry out a mutagenesis using these transposons. Furthermore, the insertion sequence IS31831 was isolated from *Corynebacterium glutamicum* ATCC 31831 (Vertes et al., Molecular Microbiology (1994) 11: 739–746). The artificial transposon Tn31831 was constructed by combining IS31831 with the kanamycin-resistance gene aphA (Vertes et al., Molecular and General Genetics (1994) 245: 397–405). Vertes et al. (Molecular and General Genetics (1994) 245: 397–405) and Jaeger et al. (FEMS Microbiology Letters (1995) 126: 1–6) demonstrated the application of these transposons in the strains *Brevibacterium flavum* MJ233C and *Corynebacterium glutamicum* ATCC 13058.

Another transposon is the transposon Tn5531 which is described in Ankri et al. (Journal of Bacteriology (1996) 178: 4412–4419) and used by way of example during the course of the present invention. To this end, in a particular embodiment of the present invention, the *Corynebacterium glutamicum* strain ATCC 14752 is subjected to an appropriate mutagenesis. Optionally it is also possible to use the *Corynebacterium glutamicum* strain ATCC 13032. The transposon Tn5531 contains the aph3 kanamycin-resistance gene and can be administered in the form of the plasmid vector pCGL0040 (FIG. 1). The nucleotide sequence of the transposon Tn5531 is freely available under accession number U53587 at the National Center for Biotechnology Information (NCBI, Bethesda, Md., USA). Listing the aforementioned transposons characterizes the present invention in more detail without limiting it.

Following transposon mutagenesis, a mutant defective in the desired gene(s) is selected. According to the invention, a mutant defective in the serB and/or serC genes is recognized by growing well on minimal medium containing L-serine but growing poorly on minimal medium without L-serine.

The appropriately selected defective mutants of strains of coryneform bacteria are then used for cloning and sequencing the serB and serC genes.

The genes may be cloned, for example, by complementing the defective mutants. To this end, a gene library of the DNA of the coryneform bacterium to be studied is generated. The generating of gene libraries is described in generally known textbooks and manuals. Examples which may be mentioned are the textbook by Winnacker: Gene und Klone, Eine Einfuhrung in die Gentechnologie (Verlag Chemie, Weinheim, Germany, 1990) and the manual by Sambrook et al.: Molecular Cloning, A Laboratory Manual (Cold Spring Harbor Laboratory Press, 1989). Bathe et al. (Molecular and General Genetics, 252: 255–265, 1996) describe a *Corynebacterium glutamicum* ATCC 13032 gene library which was generated with the aid of the cosmid vector SuperCos I (Wahl et al., 1987, Proceedings of the National Academy of Sciences USA, 84: 2160–2164) in the *E. coli* K-12 strain NM554 (Raleigh et al., 1988, Nucleic Acids Research 16: 1563–1575). Vectors suitable according to the invention are those replicating in coryneform bacteria, preferably *Corynebacterium glutamicum*. Vectors of this kind are known in the art. An example which may be mentioned is the plasmid vector pZ1 described in Menkel et al. (Applied and Environmental Microbiology (1989) 64: 549–554).

The gene library is then transferred into the above-described bacterial strain having a defective serB or serC gene by means of transformation, according to the invention preferably by electroporation. Using methods known per se, those transformed bacteria are selected, which have the ability to grow on minimal medium in the absence of L-serine. The DNA fragments of the originally used gene library are re-isolated from said selected transformants and can then be subjected to a sequence analysis.

In another embodiment of the present invention, it is possible, due to the defective mutants of a coryneform bacterium generated by mutagenesis using the transposon Tn5531, such as, for example, the strains ATCC 14752serB:: Tn5531 and ATCC 14752serC::Tn5531, to clone and isolate the serB::Tn5531 allele and the serC::Tn5531 allele, respectively, directly by utilizing the kanamycin-resistance gene aph3 contained in the transposon. To this end, known cloning vectors such as, for example, pUC18 (Norrander et al., Gene (1983) 26: 101–106 and Yanisch-Perron et al., Gene (1985) 33: 103–119) or pGEM-T (Zhou M-Y, Clark S E and Gomez-Sanchez C E (1995) BioTechniques 19: 34; Kobs G (1995) Promega Notes 55: 28; Promega Cooperation, Madison, USA), are used. Host systems suitable for cloning are in particular those *Escherichia coli* strains which are restriction and recombination defective. An example of these is the strain DH5αmcr which has been described by Grant et al. (Proceedings of the National Academy of Sciences USA, 87 (1990) 4645–4649). Transformants are selected in the presence of kanamycin.

The DNA isolated from the transformants obtained, which contains the genes of interest, is then sequenced. To this end, the dideoxy chain termination method described by Sanger et al. (Proceedings of the National Academy of Sciences of the United States of America USA (1977) 74: 5463–5467) can be employed. Thereafter, the genes present upstream and downstream of the Tn5531 insertion site are obtained. The nucleotide sequences obtained are then analyzed and assembled using commercially available sequence analysis programs such as, for example, the Laser gene program package (Biocomputing Software for Windows, DNASTAR, Madison, USA) or the HUSAR program package (Release 4.0, EMBL, Heidelberg, Germany). The inventive nucleic acids of the serB and serC genes of coryneform bacteria were isolated and their sequences were determined in the manner described above.

Surprisingly, homology comparisons with known sequences revealed that the serB-encoded polypeptide is moderately similar to *Escherichia coli* phosphoserine phosphatase, while the polypeptide derived from serC has only low, albeit significant, similarity to *Escherichia coli* phosophoserine aminotransferase. Likewise, the corynebacterial genes found have only low to moderate similarities to known phosphoserine phosphatases and phosphoserine aminotransferases from other organisms (e.g. yeast). Only the polypeptide sequences derived from the putative *Mycobacterium tuberculosis* serB and serC genes display high similarity to the corynebacterial proteins. Table 2 depicts the result of such a homology comparison. In addition, the nucleotide sequence of the coryneform genes reveals that the PCR primers used in EP 0 931 833, although suitable for amplifying the *Escherichia coli* genes, are unsuitable for isolating the coryneform serB and serC genes, due to said low sequence similarity.

This once more elucidates the advantage of the inventive method of transposon mutagenesis for cloning the genes serB and serC from coryneform bacteria.

The present invention additionally relates to a method for the microbial production of L-serine, in which at least one of the nucleic acids of the invention, isolated from a coryneform bacterium, is transferred into a homologous microorganism and expressed there, with gene expression and/or activity of the correspondingly encoded polypeptide being increased compared to the correspondingly genetically unmodified microorganism, this genetically modified microorganism is used for the fermentative production of L-serine and the L-serine formed accordingly is isolated from the culture medium.

Another variant of the present invention comprises a method for the improved microbial production of L-serine, in which a) at least one nucleic acid coding for a phosphoserine phosphatase (serB) and/or phosphoserine aminotransferase (serC) according to SEQ ID No. 1, 3, 5 and/or 7 and a nucleic acid according to SEQ ID No. 9 or 11 or alleles thereof or derivatives therefrom, isolated from a coryneform bacterium, are transferred into a homologous microorganism and expressed therein, and expression and/or lifespan of the nucleic acids and/or activity and/or lifespan of the correspondingly encoded polypeptides are increased compared to the correspondingly genetically unmodified microorganism, b) this genetically modified microorganism from step a) is used for the fermentative production of L-serine, L-serine being increasingly secreted into the culture medium, and c) the L-serine correspondingly formed is isolated from the culture medium.

Key to the sequence listing, figures and tables

Sequence listing:

Representation of the nucleic acid sequences containing the genes serB (SEQ ID No. 1), serC (SEQ ID No. 3) and thrE (SEQ ID No. 9) and of the amino acid sequences derived therefrom, SerB (SEQ ID No. 2), SerC (SEQ ID No. 4) and ThrE (SEQ ID No. 10) from *Corynebacterium glutamicum* ATCC 14752 and *Corynebacterium glutamicum* ATCC 13032 (corresponding to SEQ ID No. 5, 7, 6, 8, 11 and 12).

BRIEF DESCRIPTION OF THE DRAWINGS AND THE TABLES

FIG. 1: Schematic representation of the vector pCGLO04O

The meaning of the abbreviations used is as follows:

Amp=β-lactamase gene which imparts resistance to ampicillin

Kan=phosphotransferase gene which imparts resistance to kanamycin

Cleavage sites of restriction endonucleases are also indicated.

Figure 2:
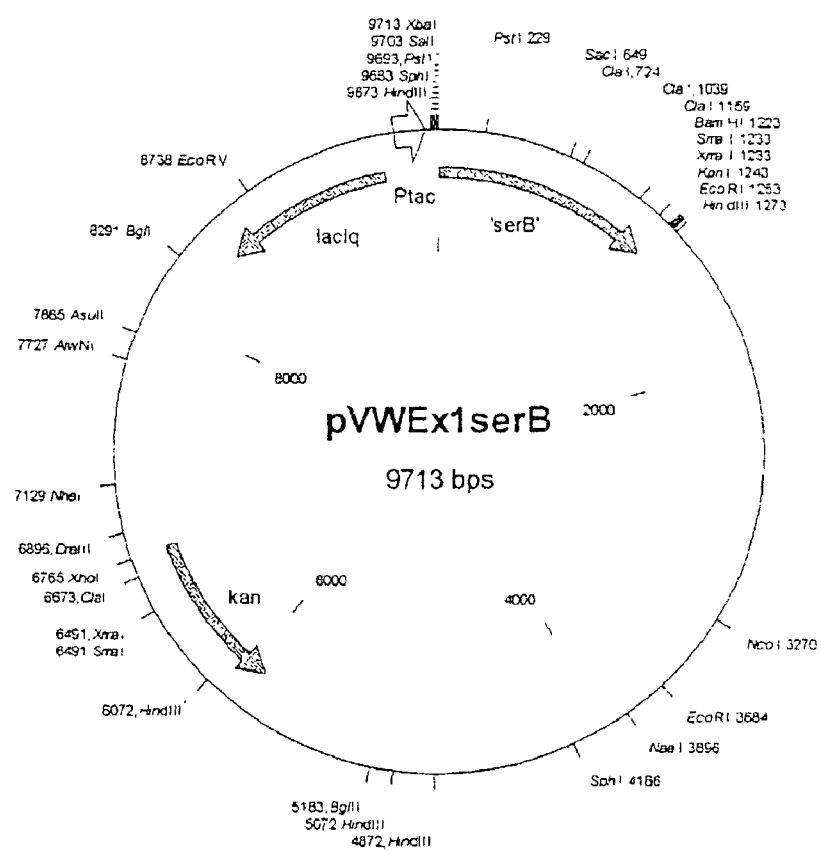

FIG. 2: Schematic representation of the vector pVWEx1serB

The meaning of the abbreviations used is as follows:

Kan=phosphotransferase gene which imparts resistance to kanamycin lacI$^q$=quantitatively expressed repressor of the *E. coil* lactose operon P$^{tac}$=IPTG-inducible artificial promoter composed of the trp promoter and the lac promoter of *E. coil*

Cleavage sites of restriction endonucleases are also indicated

Figure 3:
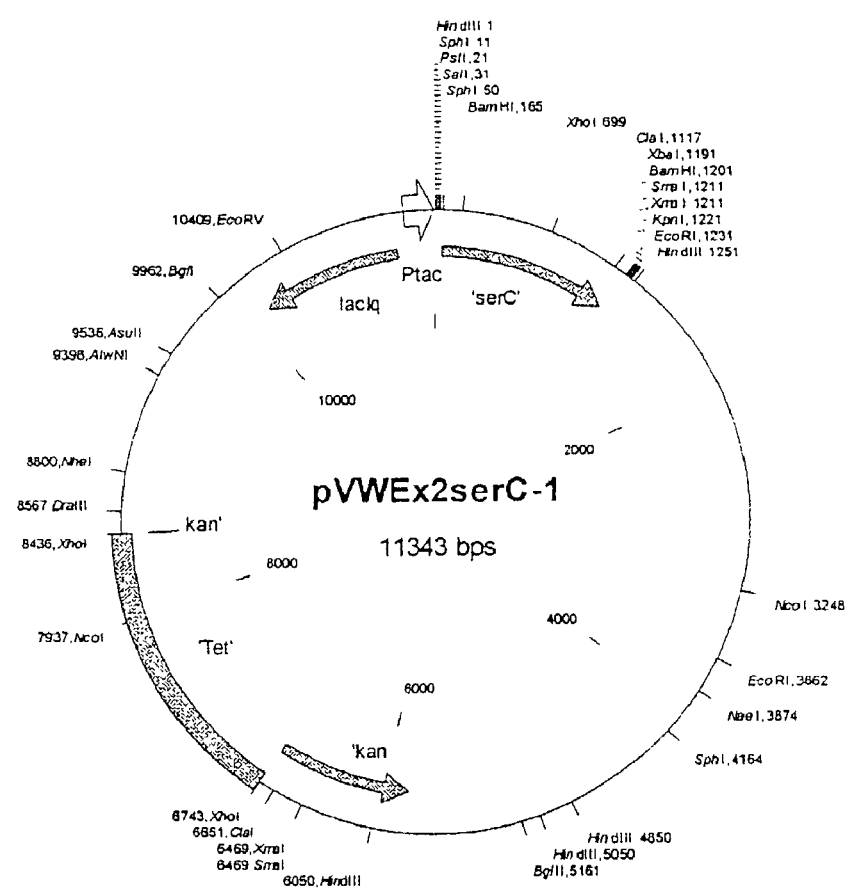

FIG. 3: Schematic representation of the vector pVWEx1serC-1

The meaning of the abbreviations used is as follows:

Kan=phosphotransferase gene which imparts resistance to kanamycin

Tet=tetα1 gene of plasmid pHY163PLK (Ishiwa & Shibahara, 1985, Jpn. J. Cenet., 60: 485–498), which imparts resistance to tetracycline lacI$^q$=quantitatively expressed repressor of the *E. coil* lactose operon p$^{tac}$=IPTO-inducible artificial promoter composed of the trp promoter and the lac promoter of *E. coli*

Cleavage sites of restriction endonucleases are also indicated

Table 1: Composition of the CGXII mineral-salt medium for culturing coryneform bacteria Table 2: Comparison of the similarities of phosphoserine aminotransferase (PSAT; serC) and phosphoserine phosphatase (PSP; serB) of *Corynebacterium giutamicum* to known phosphoserine aminotransferases and phosphoserme phosphatases of other organisms Table 3: Comparative overview of the accumulation of L-serine in the culture supernatant of *Corynebacterium giutamicum* wild type ATCC 13032 and of the *Corynebacterium giutamicum* strains ATCC 13032(pVWEX1), ATCC 13032(pVWEX1serB) and ATCC 13032 (pVWEX2serC) transformed with the corresponding plasmids In order to achieve an increased gene expression (overexpression) in a genetically engineered organism, the copy number of the appropriate genes may be increased. Furthermore, the promoter and/or regulatory regions and/or the ribosomal binding site which is located upstream of the structural gene can be modified accordingly so that the rate of expression is increased. Expression cassettes which are incorporated upstream of the structural gene act in a similar way. Additionally, inducible promoters make it possible to increase expression during the course of the fermentative production of L-serine. Expression is likewise improved by measures to extend the lifespan of the mRNA. The genes or gene constructs may be either present in plasmids with varying copy number or integrated and amplified in the chromosome. Furthermore, the enzyme activity itself may be increased or enhanced by preventing degradation of the enzyme protein. As an alternative, it is further possible to achieve overexpression of the relevant genes by modifying the medium composition and management of the culture.

Instructions for this can be found by the skilled worker, inter alia, in Martin et al., (Bio/Technology 5, 137–146 (1987)), in Guerrero et al. (Gene 138, 35–41 (1994)), Tsuchiya and Morinaga (Bio/Technology 6, 428–430 (1988)), in Eikmanns et al. (Gene 102, 93–98 (1991)), in the European patent EPS 0 472 869, in U.S. Pat. No. 4,601,893, in Schwarzer and Pühler (Bio/Technology 9, 84–87 (1991), in Reinscheid et al. (Applied and Environmental Microbiology 60, 126–132 (1994)), in LaBarre et al. (Journal of Bacteriology 175, 1001–1007 (1993)), in the patent application WO 96/15246, in Malumbres et al. (Gene 134, 15–24 (1993)), in the Japanese patent JP-A-10–229891, in Jensen and Hammer (Biotechnology and Bioengineering 58, 191–195 (1998)), in Makrides (Microbiological Reviews 60: 512–538 (1996)) and in well-known textbooks of genetics and molecular biology.

The genetically modified microorganisms prepared according to the invention may be cultured for the purpose of producing L-serine continuously or in a batch process or in a fed batch or repeated fed batch process. A review of known culturing methods can be found in the textbook by Chmiel (Bioprozesstechnik 1. Einfuhrung in die Bioverfahrenstechnik (Gustav Fischer Verlag, Stuttgart, 1991)) or in the textbook by Storhas (Bioreaktoren und periphere Einrichtungen (Vieweg Verlag, Brunswick/Wiesbaden, 1994)).

The culture medium to be used must satisfy the requirements of the particular strains in a suitable manner. The manual "Manual of Methods for General Bacteriology" of the American Society for Bacteriology (Washington D.C., USA, 1981) contains descriptions of culture media for various microorganisms. Carbon sources which may be used are sugars and carbohydrates such as, for example, glucose, sucrose, lactose, fructose, maltose, molasses, starch and cellulose, oils and fats such as, for example, soybean oil, sunflower oil, peanut oil and coconut fat, fatty acids such as, for example, palmitic acid, stearic acid and linoleic acid, alcohols such as, for example, glycerol and ethanol and organic acids such as, for example, acetic acid. These substances may be used individually or in a mixture. Nitrogen sources which may be used are compounds containing organic nitrogen, such as peptone, yeast extract, meat extract, malt extract, corn steep liquor, soybean meal and urea, or inorganic compounds such as ammonium sulfate, ammonium chloride, ammonium phosphate, ammonium carbonate and ammonium nitrate. The nitrogen sources may be used individually or as a mixture. Phosphorus sources which may be used are phosphoric acid, potassium dihydrogen phosphate or dipotassium hydrogen phosphate or the corresponding sodium salts. The culture medium should furthermore contain metal salts such as, for example, magnesium sulfate or iron sulfate, which are required for growth. Finally, essential growth substances such as amino acids and vitamins may be used in addition to the abovementioned substances. Moreover, suitable precursors may be added to the culture medium. Said substances for use may be introduced into the culture in the form of a single addition or fed in a suitable manner during culturing.

The pH of the culture is controlled by using basic compounds such as sodium hydroxide, potassium hydroxide, ammonia or aqueous ammonia or acidic compounds such as phosphoric acid or sulfuric acid in a suitable manner. Foaming can be controlled by using antifoams such as, for example, fatty acid polyglycol esters. Plasmid stability can be maintained by adding to the medium suitable selectively acting substances such as, for example, antibiotics. Aerobic conditions are maintained by introducing into the culture oxygen or oxygen-containing gas mixtures such as, for example, air. The culture temperature is usually from 20° C. to 45° C. and preferably from 25° C. to 40° C. Culturing is continued until a maximum amount of L-serine has been produced. This target is usually reached within 10 to 160 hours.

L-serine formation can be analyzed via anion exchange chromatography with subsequent ninhydrin derivatization, as described in Spackman et al. (Analytical Chemistry, 30, (1958), 1190), or via reversed phase HPLC, as described in Lindroth et al. (Analytical Chemistry (1979) 51: 1167–1174).

The microorganisms which are the subject of the present invention are capable of producing L-serine from glucose, sucrose, lactose, mannose, fructose, maltose, molasses, starch, cellulose or from glycerol and ethanol. They may be the representatives of coryneform bacteria already described in detail hereinbefore.

Table 3 depicts a selection of results of the fermentation. Here, the microorganisms genetically modified in accordance with the invention are distinguished by a substantially improved production of L-serine compared to the correspondingly untransformed microorganisms (wild types) or to those microorganisms merely containing the vector without gene insert.

A particular embodiment of the present invention shows that overexpression of the homologous serB gene in *C. glutamicum* ATCC 13032 (13032(pVWEx1serB)) results in an at least 4-fold increase in the accumulation of L-serine in the medium in comparison with the control strains. Overexpression of the homologous serC gene (13032 (pVWEx2serC)) can achieve an at least 20-fold increase in the accumulation of L-serine. A further increase in the production of L-serine can be expected from joint overexpression of both genes, serB and serC, in a homologous system.

In this connection, the fact that the increase in the accumulation of L-serine is achieved even by using the *Corynebacterium glutamicum* ATCC 13032 wild type is especially remarkable. The use according to the invention of a homologous amino-acid production strain may thus attain a still further increased production of L-serine.

Amino-acid production strains mean in accordance with the present invention *Corynebacterium glutamicum* strains or homologous microorganisms which have been modified by classical and/or molecular genetic methods such that their metabolic flow flows increasingly in the direction of biosynthesis of amino acids or derivatives thereof (metabolic engineering). These amino-acid production strains contain, for example, one or more genes and/or the corresponding enzymes which are in key positions of the metabolic pathway, which are crucial and, accordingly, regulated in a complex manner (bottle neck), and whose regulation has been modified or which are even deregulated. In this connection, the present invention comprises all already known amino-acid production strains, preferably of the genus *Corynebacterium* or of homologous organisms. Furthermore, the invention also comprises those production strains which can be prepared by the skilled worker using common methods and according to findings in other microorganisms, for example enterobacteria, bacillaceae or yeast species.

Furthermore, the invention also comprises those amino-acid production strains in which L-serine degradation has been modified, preferably reduced. This may be carried out, for example, by specific genetic modifications of L-serine-degrading enzymes or of the corresponding genes.

According to the invention, the yield of L-serine in the final product is further improved by considerably improving L-serine export out of the cells into the surrounding medium. According to the invention, this is achieved by increased expression of the L-threonine export carrier which, surprisingly, also transports, inter alia, the L-serine formed actively via the cell membrane. This increases the L-serine content in the culture medium still further and results in a final product of considerably improved quality compared to hitherto known products.

The present invention also comprises bacterial strains which, in addition to the advantageous properties regarding the production of L-serine, have an improved ability to export L-serine out of the cells into the culture medium. In this connection, preference is given to bacteria having an increased content of membrane transport proteins such as, for example, an L-amino acid-specific export carrier, in particular the L-threonine export carrier.

The present invention further relates to the use of a genetically modified microorganism of the above-described type for the production of L-serine and/or secondary products thereof according to a method of the type described at the beginning.

The present invention further relates to the use of the L-amino acids prepared in the above-described manner for use in the food, animal feed and/or pharmaceutical industries or in human medicine. In addition, the amino acid L-serine prepared according to the invention can be used as a precursor for the synthesis of L-glycine, L-cysteine and/or L-tryptophan and/or of metabolic products derivable therefrom.

EXAMPLES

The examples below illustrate the present invention in more detail but are not limiting:

General Techniques:

Isolation of plasmid DNA from *Escherichia coli* and all techniques regarding restriction, Klenow treatment and alkaline phosphatase treatment were carried out according to Sambrook et al. (Molecular cloning. A laboratory manual (1989) Cold Spring Harbor Laboratory Press). *Escherichia coli* were transformed according to Chung et al. (Proceedings of the National Academy of Sciences of the United States of America USA (1989) 86: 2172–2175), unless described otherwise.

Cloning and Sequencing of the *Corynebacterium glutamicum* ATCC 14752 serB and serC Genes 1. Transposon Mutagenesis The *Corynebacterium glutamicum* strain ATCC 14752 was subjected to a mutagenesis using the transposon Tn5531 whose sequence has been deposited under accession number U53587 in the nucleotide database of the National Center for Biotechnology Information (Bethesda, USA). The plasmid pCGL0040 which contains the assembled transposon Tn5531 (Ankri et al., Journal of Bacteriology (1996) 178: 4412–4419) was isolated from the methylase-defective *Escherichia coli* strain GM2929pCGL0040 (*Escherichia coli* GM2929: Palmer et al., Gene (1994) 143: 1–12). The *Corynebacterium glutamicum* strain ATCC 14752 was transformed with the plasmid pCGL0040 by means of electroporation (Haynes et al., FEMS Microbiology Letters (1989) 61: 329–334). Clones which had the transposon Tn5531 integrated into their genome were identified on the basis of their resistance to kanamycin on LBHIS agar plates containing 15 µg/ml kanamycin (Liebl et al., FEMS Microbiology Letters (1989) 65: 299–304). In this manner, 1800 clones were obtained which were tested for delayed growth in the presence of seryl-alanine. For this purpose, all clones were transferred individually to CGXII minimal medium agar plates with and without 2 mM seryl-alanine. The medium was identical to the CGXII medium described in Keilhauer et al. (Journal of Bacteriology (1993) 175: 5593–5603) but contained additionally 25 µg/ml kanamycin and 15 g/l agar. Table 1 depicts the composition of the medium described by Keilhauer et al.

The agar plates were incubated at 30° C. and growth was examined after 12, 18 and 24 hours. Two transposon mutants were obtained which grew in the presence of seryl-alanine in a manner comparable to the starting strain *Corynebacterium glutamicum* ATCC 14752 but which showed no growth in the absence of seryl-alanine. The mutants also grew in the presence of serine alone, proving that they are serine-auxotrophic mutants which must have a defect in serine metabolism. These mutants were referred to as ATCC 14752ser1::Tn5531 and ATCC 14752ser2::Tn5531.

2. Cloning and Sequencing of the Tn5531 Insertion Sites in ATCC 14752ser1::Tn5531 and ATCC 14752ser2::Tn5531

In order to clone the insertion sites in the mutants described, which are located upstream of the transposon Tn5531, first the chromosomal DNA of these mutant strains was isolated as described in Schwarzer et al. (Bio/Technology (1990) 9: 84–87) and 400 ng thereof were cleaved using the restriction endonuclease XbaI. The entire restriction mixture was ligated into the pUC18 vector (Norander et al., Gene (1983) 26: 101–106) from Roche Diagnostics (Mannheim, Germany), which had likewise been linearized using XbaI. The entire ligation mixture was used to transform the *Escherichia coli* strain DH5αmcr (Grant et al., Proceedings of the National Academy of Sciences of the United States of America USA (1990) 87: 4645–4649) by means of electroporation (Dower et al., Nucleic Acid Research (1988) 16: 6127–6145). Transformants which contained the cloned transposon Tn5531 insertion sites on the pUC18 vector were identified on the basis of their resistance to carbenicillin and kanamycin on LB agar plates containing 50 µg/ml carbenicillin and 25 µg/ml kanamycin. Plasmids were prepared in each case from three transformants and the sizes of the cloned inserts were determined by restriction analysis. The nucleotide sequences of the insertion sites on the plasmids, which contained an approx. 10 kb insert in the case of ser1::Tn5531 and a 4.5 kb insert in the case of ser2::Tn5531, were determined according to the dideoxy chain termination method of Sanger et al. (Proceedings of the National Academy of Sciences of the United States of America USA (1977) 74: 5463–5467). To this end, first in each case approx. 600 bp of the two inserts were sequenced, starting from the following oligonucleotide primer: SEQ ID NO. 13: 5'-CGG GTC TAC ACC GCT AGC CCA GG-3'. Sequence extensions were then carried out in each case by means of primer walking so that it was possible to sequence in total approx. 1.4 kb of the ser1::Tn5531 insert and 1.2 kb of the ser2::Tn5531 insert, respectively. The Laser gene program package (Biocomputing Software for Windows, DNASTAR, Madison, USA) analysis revealed that in both cases the transposon had been inserted into the start of an open reading frame.

The insertion sites located downstream of the transposon were identified by cleaving the chromosomal DNA of the mutants with the restriction endonuclease EcoRI followed by ligation into the EcoRI-linearized pUC18 vector. Further cloning was carried out as described above. The nucleotide sequences of the insertion sites on one of the plasmids having an approx. 6.5 kb insert starting from ser1::Tn5531 and, respectively, on one of the plasmids having an approx. 5.0 kb insert starting from ser2::Tn5531 were determined according to the dideoxy chain termination method of Sanger et al. (Proceedings of the National Academy of Sciences of the United States of America USA (1977) 74: 5463–5467). To this end, approx. 400 bp of the ser1::TN5531 insert and approx. 220 bp of the ser2::Tn5531 insert, respectively, were sequenced starting from the following oligonucleotide primer: SEQ ID NO. 14: 5'-CGG TGC CTT ATC CAT TCA GG-3'.

The nucleotide sequences obtained were analyzed and assembled using the Laser gene program package (Biocomputing Software for Windows, DNASTAR, Madison, USA). The nucleotide sequences are depicted as SEQ ID No. 1 and SEQ ID No. 3. The analysis identified in each case an open reading frame of 1209 bp for ser1::Tn5531, the corresponding gene being referred to as serB, and of 1128 bp for ser2::Tn5531, the corresponding gene being referred to as serC. The corresponding gene products comprise 403 and 376 amino acids, respectively, and are depicted as SEQ ID No. 2 and SEQ ID No. 4, respectively.

Cloning and Sequencing of the serB and serC Genes from *Corynebacterium glutamicum* ATCC 13032

The genes serB and serC were cloned into the *Escherichia coli* cloning vector pGEM-T (Zhou M-Y, Clark S E and Gomez-Sanchez C E (1995) BioTechniques 19: 34; Kobs G (1995) Promega Notes 55: 28; Promega Cooperation, Madison, USA). Cloning was carried out in two steps. First, the genes from *Corynebacterium glutamicum* ATCC 13032 were in each case amplified using a polymerase chain reaction (PCR) by means of the following oligonucleotide primers derived from SEQ ID No. 1 and SEQ ID No. 3, respectively.

```
serB-forward:
SEQ ID NO. 15: 5'-GCAGAGGCACACACTGGAC-3' serB-reverse:
SEQ ID NO. 16: 5'-CTTGAGGAGGAGGTGGGC-3' serC-forward:
SEQ ID NO. 17: 5'-CATCGTTTGGGAGACTGCG-3' serC-reverse:
SEQ ID NO. 18: 5'-CGTACTGGTGTAACTGTACGGG-3'.
```

The PCR reaction was carried out in 30 cycles in the presence of 200 μM deoxynucleotide triphosphates (dATP, dCTP, dGTP, dTTP), in each case 1 μM of the appropriate oligonucleotide, 100 ng of chromosomal DNA from *Corynebacterium glutamicum* ATCC 13032, 1/10 volume of 10 times reaction buffer and 2.6 units of a heat-stable Taq/Pwo DNA polymerase mixture (Expand High Fidelity PCR System from Roche Diagnostics, Mannheim, Germany) in a thermocycler (PTC-100, MJ Research, Inc., Watertown, USA) under the following conditions: 94° C. for 60 seconds, 56° C. for 90 seconds and 72° C. for 2 minutes.

The amplified, about 1.7 kb sized serB fragment and the amplified, about 1.3 kb sized serC fragment were then ligated with the pGEM-T vector with the aid of the Promega PCR Cloning Kit according to the manufacturer's instructions. The *Escherichia coli* strain DH5αmcr (Grant et al., Proceedings of the National Academy of Sciences of the United States of America USA (1990) 87: 4645–4569) was transformed with both ligation mixtures. Transformants were identified on the basis of their resistance to ampicillin on LB agar plates containing 50 μg/ml ampicillin. Plasmids were prepared from in each case 10 transformants and tested for the presence of the 1.7 kb and, respectively, 1.3 kb PCR fragments as inserts by restriction analysis. The recombinant plasmids produced in this way are referred to as pGEM-TserB and pGEM-TserC below.

The nucleotide sequences of the 1.7 kb and 1.3 kb PCR fragments in plasmid pGEM-TserBexp and plasmid pGEM-TserCexp, respectively, were determined according to the dideoxy chain termination method of Sanger et al. (Proceedings of the National Academy of Sciences of the United States of America USA (1977) 74: 5463–5467). To this end, the complete inserts of pGEM-TserB and pGEM-TserC were sequenced with the aid of the following primers from Roche Diagnostics (Mannheim, Germany).

```
Universal primer:
SEQ ID NO. 19: 5'-GTA AAA CGA CCC CCA GT-3'

Reverse primer:
SEQ ID NO. 20: 5'-GGA AAC AGC TAT GAC CAT G-3'
```

SEQ ID No. 5 depicts the nucleotide sequence of the insert in plasmid pGEM-TserB, and SEQ ID No. 7 depicts the nucleotide sequence of the insert in plasmid pGEM-TserC. The nucleotide sequence obtained was analyzed using the Laser gene program package (Biocomputing Software for Windows, DNASTAR, Madison, USA). The analysis identified in each case an open reading frame of 1209 bp and 1128 bp in length, respectively. The corresponding genes were referred to as serB and serC. The corresponding gene products code for polypeptides of 403 and, respectively, 376 amino acids in length, which are depicted in SEQ ID No. 6 and SEQ ID No. 8, respectively.

Overexpression of the Genes for Phosphoserine Phosphatase, serB, and Phosphoserine Aminotransferase, serC The effect of overexpressing the genes for phosphoserine phosphatase, serB, and phosphoserine aminotransferase, serC on the production of serine was studied by using the expression vectors pVWEX1 (Wendisch, V., Dissertation Heinrich-Heine Universitat, Düsseldorf, 1997; imparts a resistance to kanamycin) and pVWEX2 (Wendisch, V., PhD thesis, Heinrich-Heine Universitat, Dusseldorf, 1997; imparts a resistance to tetracycline) which allow IPTG-inducible expression (Molecular Cloning, A laboratory manual (1989) Cold Spring Harbor Laboratory Press). The serB gene was cloned into the pVWEX1 vector and the serC gene was cloned into the pVWEX2 vector, both without their respective promoters. For this purpose, the following primers were synthesized first:

```
serB-exp-for:
SEQ ID NO. 21: 5'-ATCTAGAATGATCACAGTGAGCCGTAAAG-3' serB-exp-rev:
SEQ ID NO. 22: 5'-AGGATCCTTAGGCATTTGTCAATGGAACGC-3' serC-exp-for:
SEQ ID NO. 23: 5'-AGCATGCATGCCCGAAGACATGACCG-3' serC-exp-rev:
SEQ ID NO. 24: 5'-ATCTAGATTACTTCCTTGCAAAACCGC-3'
```

The promoterless serB gene was amplified as a 1226 bp fragment (SEQ ID No. 5, bases 382 to 1594) and the promoterless serC gene as a 1157 bp fragment (SEQ ID No. 7, bases 132 to 1261) from chromosomal DNA of *Corynebacterium glutamicum* ATCC 13032 by means of PCR. The primers were chosen for the primer serB-exp-for to mediate an XbaI cleavage site, for the primer serB-exp-rev to mediate a BamHI cleavage site, for the primer serC-exp-for to mediate an SphI cleavage site and for the primer serC-exp-rev to mediate an XbaI cleavage site. The isolated PCR products were, as described above, first cloned into the pGEM-T vector, resulting in the plasmids pGEM-TserB-exp and PGEM-TserC-exp. Subsequently, the promoterless serB gene was excised from the vector pGEM-TserBexp by means of XbaI-BamHI restriction digest and ligated into the pVWEX1 vector linearized correspondingly with XbaI-BamHI. After an SpeI-XbaI restriction digest, the promoterless serC gene was excised from the vector pGEM-TserBexp and ligated into the XbaI-linearized vector pVWEX2. The constructs obtained, pVWEX1serB (FIG. 2) and pVWEX2serC (FIG. 3) were tested by restriction digest.

Increased Accumulation of L-Serine by Overexpression of the Genes for Phosphoserine Phosphatase, serB and Phosphoserine Aminotransferase, serC The plasmids pVWEX1-serB and pVWEX2-serC were introduced, in each case individually, into the wild-type strain *Corynebacterium glutamicum* ATCC 13032 by electroporation, resulting in the strains *C. glutamicum* 13032 (pVWEX1serB) and *C. glutamicum* 13032 (pVWEX2serC). The wild-type, *Corynebacterium glutamicum* ATCC 13032, and the *C. glutamicum* strain ATCC containing the pVWEX1 vector without insert were cultured as negative controls. L-serine elimination from all of the above-mentioned strains was then determined and the results are comparatively summarized in Table 3.

For this purpose, the strains were cultivated in complex medium (2×TY; Molecular Cloning, A laboratory manual (1989) Cold Spring Harbor Laboratory Press; with 50 µg/l kanamycin, 25 µg/l tetracycline and, respectively, 50 µg/l kanamycin and 25 µg/l tetracycline), and the CGXII fermentation medium (J Bacteriol (1993) 175: 5595–5603) was inoculated, in each case separately, with the precultures. The medium additionally contained the appropriate antibiotic(s) and 200 µg/ml IPTG. After culturing on a rotary shaker at 120 revolutions per minute and at 30° C. for 24 hours, the amount of L-serine accumulated in the medium was determined. The amino-acid concentration was determined by means of high pressure liquid chromatography (J Chromat (1983) 266: 471–482).

Tables

TABLE 1

| Component | Concentration |
|---|---|
| $(NH_4)_2SO_4$ | 20 g/l |
| Urea | 5 g/l |
| $KH_2PO_4$ | 1 g/l |
| $K_2HPO_4$ | 1 g/l |
| $MgSO_4 \times 7H_2O$ | 0.25 g/l |
| 3-morpholinopropanesulfonic acid | 42 g/l |
| $CaCl_2$ | 10 mg/l |
| $FeSO_4 \times 7H_2O$ | 10 mg/l |
| $MnSO_4 \times H_2O$ | 10 mg/l |
| $ZnSO_4 \times 7H_2O$ | 1 mg/l |
| $CuSO_4$ | 0.2 mg/l |
| $NiCl_2 \times 6H_2O$ | 0.02 mg/l |
| Biotin | 0.2 mg/l |
| Glucose | 40 g/l |
| Protocatechuic acid | 30 mg/l |

TABLE 2

| | PSAT | | PSP | |
|---|---|---|---|---|
| | % Identity | % Similarity | % Identity | % Similarity |
| *Escherichia coli* | 23 | 33 | 49 | 40 |
| *Saccharomyces cerevisiae* | 27 | 36 | 36 | 49 |
| *Mycobacterium tuberculosis* | 61 | 69 | 55 | 64 |

TABLE 3

| *C. glutamicum* strain | L-serine [µM] |
|---|---|
| 13032 | ≦10 |
| 13032 (pVWEx1) | ≦10 |
| 13032 (pVWEx2) | ≦10 |
| 13032 (pVWEx1serB) | ≧40 |
| 13032 (pVWEx2serC) | ≧200 |

What is claimed is:

1. A method for the microbial production of L-serine comprising the steps of:
   a) isolating at least one nucleic acid from a coryneform bacterium, coding for a phosphoserine phosphatase (serB) or a phosphoserine aminotransferase (serC) according to one of SEQ no. 1, 3, 5, or 7 and a nucleic acid coding for an L-threonine export carrier according to one of SEQ ID NO. 9 or 11, transferring the isolated nucleic acid to a coryneform bacterium and expressing it therein, increasing the gene expression as compared to the corresponding genetically unmodified microorganism,
   b) using the genetically modified microorganism from step a) for the fermentative production of L-serine in a culture medium, and
   c) isolating the L-serine formed from the culture medium.

2. A method for the microbial production of L-serine, comprising the steps of
   a) transferring at least one nucleic acid coding for a phosphoserine phosphatase (serB) or phosphoserine aminotransferase (serC) according to SEQ ID No. 1, 3, 5, or 7 and a nucleic acid coding for an L-threonine export carrier according to SEQ ID NO. 9 or 11, isolated from a coryneform bacterium, into a coryneform bacterium and expressing them therein, increasing the gene expression as compared to the corresponding genetically unmodified microorganism,
   b) using this genetically modified microorganism from step a) for the fermentative production of L-serine, whereby L-serine is increasingly secreted into the culture medium, and
   c) isolating the L-serine formed from the culture medium.

* * * * *

SEQUENCE LISTING

<160> NUMBER OF SEQ ID NOS: 12

<210> SEQ ID NO 1
<211> LENGTH: 1765
<212> TYPE: DNA
<213> ORGANISM: C. glutamicum ATCC 14 752
<220> FEATURE:
<221> NAME/KEY: CDS
<222> LOCATION: (414)..(1613)
<223> OTHER INFORMATION: ser B (Phosphoserin-phosphatase)

<400> SEQUENCE: 1

-continued

```
atgattgaac gcatgcgcgc agaggcacac actggacatc acgatgatat taatgctcca      60
gaattgggta ccgccccagc ccttgcatct gactccagcc gctaaaagcg tctgatttaa     120
gtcggtacct gactaaataa gcaccagccc agcagagata ttctgccggg gctggtgctt     180
ttcatattcc gacttggggc accctgaat acatctcacc caattcccca taactagaca     240
attgcccagc aacgactgat aagtctccaa tgtcgtgttc cgcgctcaga catgagacaa     300
ttgttgccgt gactgaactc atccagaatg aatcccaaga atcgctgag ctggaagccg      360 gccagcaggt tgcattgcgt gaaggttatc gttatcttcc tgcggtgatc aca gtg       416
                                                              Met
                                                                1 agc ggt aaa gac cgc cca ggt gtg act gcc gcg ttc ttt agg gtc ttg      464
Ser Gly Lys Asp Arg Pro Gly Val Thr Ala Ala Phe Phe Arg Val Leu
        5                  10                 15 tcc gct aat cag gtt cag gtc ttg gac gtt gag cag tca atg ttc cgt      512
Ser Ala Asn Gln Val Gln Val Leu Asp Val Glu Gln Ser Met Phe Arg
    20                  25                  30 ggc ttt ttg aac ttg gcg gcg ttt gtg ggt atc gca cct gag cgt gtc      560
Gly Phe Leu Asn Leu Ala Ala Phe Val Gly Ile Ala Pro Glu Arg Val
35                  40                  45 gag acc gtc acc aca ggc ctg act gac acc ctc aag gtg cat gga cag      608
Glu Thr Val Thr Thr Gly Leu Thr Asp Thr Leu Lys Val His Gly Gln
 50                  55                  60                  65 tcc gtg gtg gtg gag ctg cag gaa act gtg cag tcg tcc cgt cct cgt      656
Ser Val Val Val Glu Leu Gln Glu Thr Val Gln Ser Ser Arg Pro Arg
                 70                  75                  80 tct tcc cat gtt gtt gtg gtg ttg ggt gat ccg gtt gat gcg ttg gat      704
Ser Ser His Val Val Val Val Leu Gly Asp Pro Val Asp Ala Leu Asp
             85                  90                  95 att tcc cgc att ggt cag acc ctg gcg gat tac gat gcc aac att gac      752
Ile Ser Arg Ile Gly Gln Thr Leu Ala Asp Tyr Asp Ala Asn Ile Asp
        100                 105                 110 acc att cgt ggt att tcg gat tac cct gtg acc ggc ctg gag ctg aag      800
Thr Ile Arg Gly Ile Ser Asp Tyr Pro Val Thr Gly Leu Glu Leu Lys
    115                 120                 125 gtg act gtg ccg gat gtc agc cct ggt ggt ggt gaa gcg atg cgt aag      848
Val Thr Val Pro Asp Val Ser Pro Gly Gly Gly Glu Ala Met Arg Lys
130                 135                 140                 145 gcg ctt gct gct ctt acc tct gag ctg aat gtg gat att gcg att gag      896
Ala Leu Ala Ala Leu Thr Ser Glu Leu Asn Val Asp Ile Ala Ile Glu
                150                 155                 160 cgt tct ggt ttg ctg cgt cgt tct aag cgt ctg gtg tgc ttc gat tgt      944
Arg Ser Gly Leu Leu Arg Arg Ser Lys Arg Leu Val Cys Phe Asp Cys
            165                 170                 175 gat tcc acg ttg atc act ggt gag gtc att gag atg ttg gcg gct cac      992
Asp Ser Thr Leu Ile Thr Gly Glu Val Ile Glu Met Leu Ala Ala His
        180                 185                 190 gcg ggc aag gaa gct gaa gtt gcg gca gtt act gag cgt gcg atg cgc     1040
Ala Gly Lys Glu Ala Glu Val Ala Ala Val Thr Glu Arg Ala Met Arg
    195                 200                 205 ggt gag ctc gat ttc gag gag tct ctg cgt gag cgt gtg aag gcg ttg     1088
Gly Glu Leu Asp Phe Glu Glu Ser Leu Arg Glu Arg Val Lys Ala Leu
210                 215                 220                 225 gct ggt ttg gat gcg tcg gtg atc gat gag gtc gct gcc gct att gag     1136
Ala Gly Leu Asp Ala Ser Val Ile Asp Glu Val Ala Ala Ala Ile Glu
                230                 235                 240 ctg acc cct ggt gcg cgc acc acg atc cgt acg ctg aac cgc atg ggt     1184
Leu Thr Pro Gly Ala Arg Thr Thr Ile Arg Thr Leu Asn Arg Met Gly
            245                 250                 255
```

-continued

| | |
|---|---|
| tac cag acc gct gtt gtt tcc ggt ggt ttc atc cag gtg ttg gaa ggt<br>Tyr Gln Thr Ala Val Val Ser Gly Gly Phe Ile Gln Val Leu Glu Gly<br>260     265     270 | 1232 |
| ttg gct gag gag ttg gag ttg gat tat gtc cgc gcc aac act ttg gaa<br>Leu Ala Glu Glu Leu Glu Leu Asp Tyr Val Arg Ala Asn Thr Leu Glu<br>275     280     285 | 1280 |
| atc gtt gat ggc aag ctg acc ggc aac gtc acc ggc aag atc gtt gac<br>Ile Val Asp Gly Lys Leu Thr Gly Asn Val Thr Gly Lys Ile Val Asp<br>290     295     300     305 | 1328 |
| cgc gct gcg aag gct gag ttc ctc cgt gag ttc gct gcg gat tct ggg<br>Arg Ala Ala Lys Ala Glu Phe Leu Arg Glu Phe Ala Ala Asp Ser Gly<br>310     315     320 | 1376 |
| ctg aag atg tac cag act gtc gct gtc ggt gat ggc gct aat gac atc<br>Leu Lys Met Tyr Gln Thr Val Ala Val Gly Asp Gly Ala Asn Asp Ile<br>325     330     335 | 1424 |
| gat atg ctc tcc gct gcg ggt ctg ggt gtt gct ttc aac gcg aag cct<br>Asp Met Leu Ser Ala Ala Gly Leu Gly Val Ala Phe Asn Ala Lys Pro<br>340     345     350 | 1472 |
| gcg ctg aag gag att gcg gat act tcc gtg aac cac cca ttc ctc gac<br>Ala Leu Lys Glu Ile Ala Asp Thr Ser Val Asn His Pro Phe Leu Asp<br>355     360     365 | 1520 |
| gag gtt ttg cac atc atg ggc att tcc cgc gac gag atc gat ctg gcg<br>Glu Val Leu His Ile Met Gly Ile Ser Arg Asp Glu Ile Asp Leu Ala<br>370     375     380     385 | 1568 |
| gat cag gaa gac ggc acc ttc cac cgc gtt cca ttg aca aat gcc<br>Asp Gln Glu Asp Gly Thr Phe His Arg Val Pro Leu Thr Asn Ala<br>390     395     400 | 1613 |
| taaagattcg cttctcgacg cccacctcct cctcaaggcc cgggctagcg acgggccaca | 1673 |
| tagcgaggat ccttcggatc cttcgaccgt tcaggcaatg cagatcgcgt tgcaacttcc | 1733 |
| gaaacagaat ccgccccggc ggacagatgt gc | 1765 |

<210> SEQ ID NO 2
<211> LENGTH: 400
<212> TYPE: PRT
<213> ORGANISM: C. glutamicum ATCC 14 752

<400> SEQUENCE: 2

Met Ser Gly Lys Asp Arg Pro Gly Val Thr Ala Ala Phe Phe Arg Val
1     5     10     15

Leu Ser Ala Asn Gln Val Gln Val Leu Asp Val Glu Gln Ser Met Phe
    20     25     30

Arg Gly Phe Leu Asn Leu Ala Ala Phe Val Gly Ile Ala Pro Glu Arg
  35     40     45

Val Glu Thr Val Thr Thr Gly Leu Thr Asp Thr Leu Lys Val His Gly
50     55     60

Gln Ser Val Val Glu Leu Gln Glu Thr Val Gln Ser Ser Arg Pro
65     70     75     80

Arg Ser Ser His Val Val Val Leu Gly Asp Pro Val Asp Ala Leu
    85     90     95

Asp Ile Ser Arg Ile Gly Gln Thr Leu Ala Asp Tyr Asp Ala Asn Ile
    100     105     110

Asp Thr Ile Arg Gly Ile Ser Asp Tyr Pro Val Thr Gly Leu Glu Leu
  115     120     125

Lys Val Thr Val Pro Asp Val Ser Pro Gly Gly Glu Ala Met Arg
130     135     140

Lys Ala Leu Ala Ala Leu Thr Ser Glu Leu Asn Val Asp Ile Ala Ile

```
145                 150                 155                 160
Glu Arg Ser Gly Leu Leu Arg Arg Ser Lys Arg Leu Val Cys Phe Asp
                165                 170                 175
Cys Asp Ser Thr Leu Ile Thr Gly Glu Val Ile Glu Met Leu Ala Ala
            180                 185                 190
His Ala Gly Lys Glu Ala Glu Val Ala Ala Val Thr Glu Arg Ala Met
        195                 200                 205
Arg Gly Glu Leu Asp Phe Glu Glu Ser Leu Arg Glu Arg Val Lys Ala
    210                 215                 220
Leu Ala Gly Leu Asp Ala Ser Val Ile Asp Glu Val Ala Ala Ala Ile
225                 230                 235                 240
Glu Leu Thr Pro Gly Ala Arg Thr Thr Ile Arg Thr Leu Asn Arg Met
                245                 250                 255
Gly Tyr Gln Thr Ala Val Val Ser Gly Gly Phe Ile Gln Val Leu Glu
            260                 265                 270
Gly Leu Ala Glu Glu Leu Glu Leu Asp Tyr Val Arg Ala Asn Thr Leu
        275                 280                 285
Glu Ile Val Asp Gly Lys Leu Thr Gly Asn Val Thr Gly Lys Ile Val
    290                 295                 300
Asp Arg Ala Ala Lys Ala Glu Phe Leu Arg Glu Phe Ala Ala Asp Ser
305                 310                 315                 320
Gly Leu Lys Met Tyr Gln Thr Val Ala Val Gly Asp Gly Ala Asn Asp
                325                 330                 335
Ile Asp Met Leu Ser Ala Gly Leu Gly Val Ala Phe Asn Ala Lys
            340                 345                 350
Pro Ala Leu Lys Glu Ile Ala Asp Thr Ser Val Asn His Pro Phe Leu
        355                 360                 365
Asp Glu Val Leu His Ile Met Gly Ile Ser Arg Asp Glu Ile Asp Leu
    370                 375                 380
Ala Asp Gln Glu Asp Gly Thr Phe His Arg Val Pro Leu Thr Asn Ala
385                 390                 395                 400

<210> SEQ ID NO 3
<211> LENGTH: 1469
<212> TYPE: DNA
<213> ORGANISM: C. glutamicum ATCC 14 752
<220> FEATURE:
<221> NAME/KEY: CDS
<222> LOCATION: (246)..(1373)
<223> OTHER INFORMATION: ser C  (Phosphoserin-phosphatase)

<400> SEQUENCE: 3
ttaacaacct agaaattgaa aactttgcaa aactttgagc tacccccaaa ttggtggctg      60
gtcaactaat ccccgcgttt tcaatagttc ggtgtcgcca gttttgggcg tttttcatcg     120
tttgggagac tgcgtgaaga atctagggtg ctaggaactg acagcttcag ggttatagtt     180
gttgggtcag atcgttaacg atccctggcc cttttacttc caagcgcaga agttgcccg      240 aagac atg acc gac ttc ccc acc ctg ccc tct gag ttc atc cct ggc gac     290
      Met Thr Asp Phe Pro Thr Leu Pro Ser Glu Phe Ile Pro Gly Asp
      1               5                   10                  15 ggc cgt ttc ggc tgc gga cct tcc aag gtt cga cca gaa cag att cag       338
Gly Arg Phe Gly Cys Gly Pro Ser Lys Val Arg Pro Glu Gln Ile Gln
            20                  25                  30 gct att gtc gac gga tcc gca tcc gtc atc ggt acc tca cac cgt cag       386
Ala Ile Val Asp Gly Ser Ala Ser Val Ile Gly Thr Ser His Arg Gln
        35                  40                  45
```

```
ccg gca gta aaa aac gtc gtg ggt tca atc cgc gag gga ctc tcc gac        434
Pro Ala Val Lys Asn Val Val Gly Ser Ile Arg Glu Gly Leu Ser Asp
         50                  55                  60 ctc ttc tcc ctt cca gaa ggc tac gag atc atc ctt tcc cta ggt ggt        482
Leu Phe Ser Leu Pro Glu Gly Tyr Glu Ile Ile Leu Ser Leu Gly Gly
     65                  70                  75 gcg acc gca ttc tgg gat gca gca acc ttc gga ctc att gaa aag aag        530
Ala Thr Ala Phe Trp Asp Ala Ala Thr Phe Gly Leu Ile Glu Lys Lys
 80                  85                  90                  95 tcc ggt cac ctt tct ttc ggt gag ttc tcc tcc aag ttc gca aag gct        578
Ser Gly His Leu Ser Phe Gly Glu Phe Ser Ser Lys Phe Ala Lys Ala
                 100                 105                 110 tct aag ctt gct cct tgg ctc gac gag cca gag atc gtc acc gca gaa        626
Ser Lys Leu Ala Pro Trp Leu Asp Glu Pro Glu Ile Val Thr Ala Glu
             115                 120                 125 acc ggt gac tct ccg gcc cca cag gca ttc gaa ggc gcc gat gtt att        674
Thr Gly Asp Ser Pro Ala Pro Gln Ala Phe Glu Gly Ala Asp Val Ile
         130                 135                 140 gca tgg gca cac aac gaa acc tcc act ggc gcc atg gtt cca gtt ctt        722
Ala Trp Ala His Asn Glu Thr Ser Thr Gly Ala Met Val Pro Val Leu
 145                 150                 155 cgc ccc gaa ggc tct gaa ggc tcc ctg gtt gcc att gac gca acc tcc        770
Arg Pro Glu Gly Ser Glu Gly Ser Leu Val Ala Ile Asp Ala Thr Ser
160                 165                 170                 175 ggc gct ggt gga ctg cca gta gac atc aag aac tcc gat gtt tac tac        818
Gly Ala Gly Gly Leu Pro Val Asp Ile Lys Asn Ser Asp Val Tyr Tyr
                 180                 185                 190 ttc tcc cca cag aag tgc ttc gca tcc gac ggt ggc ctg tgg ctt gca        866
Phe Ser Pro Gln Lys Cys Phe Ala Ser Asp Gly Gly Leu Trp Leu Ala
             195                 200                 205 gcg atg agc cca gca gct ctc gag cgc atc gag aag atc aac gct tcc        914
Ala Met Ser Pro Ala Ala Leu Glu Arg Ile Glu Lys Ile Asn Ala Ser
         210                 215                 220 gat cgc ttc atc cct gag ttc ctc aac ctg cag acc gca gtg gat aac        962
Asp Arg Phe Ile Pro Glu Phe Leu Asn Leu Gln Thr Ala Val Asp Asn
 225                 230                 235 tcc ctg aag aac cag acc tac aac acc cca gct gtt gct acc ttg ctg       1010
Ser Leu Lys Asn Gln Thr Tyr Asn Thr Pro Ala Val Ala Thr Leu Leu
240                 245                 250                 255 atg ctg gac aac cag gtc aag tgg atg aac tcc aac ggc ggc ctg gat       1058
Met Leu Asp Asn Gln Val Lys Trp Met Asn Ser Asn Gly Gly Leu Asp
                 260                 265                 270 gga atg gtt gct cgc acc aca gca agc tcc tcc gcc ctg tac aac tgg       1106
Gly Met Val Ala Arg Thr Thr Ala Ser Ser Ser Ala Leu Tyr Asn Trp
             275                 280                 285 gct gag gct cgc gag gag gca tcc cca tac gtg gca gat gca gct aag       1154
Ala Glu Ala Arg Glu Glu Ala Ser Pro Tyr Val Ala Asp Ala Ala Lys
         290                 295                 300 cgc tcc ctc gtt gtc ggc acc atc gac ttc gat gac tcc atc gac gca       1202
Arg Ser Leu Val Val Gly Thr Ile Asp Phe Asp Asp Ser Ile Asp Ala
 305                 310                 315 gca gtg atc gct aag ata ctg cgc gca aac ggc atc ctg gac acc gag       1250
Ala Val Ile Ala Lys Ile Leu Arg Ala Asn Gly Ile Leu Asp Thr Glu
320                 325                 330                 335 cct tac cgc aag ctg gga cgc aac cag ctg cgc atc ggt atg ttc cca       1298
Pro Tyr Arg Lys Leu Gly Arg Asn Gln Leu Arg Ile Gly Met Phe Pro
                 340                 345                 350 gcg atc gat tcc acc gat gtg gaa aag ctc acc gga gca atc gac ttc       1346
Ala Ile Asp Ser Thr Asp Val Glu Lys Leu Thr Gly Ala Ile Asp Phe
             355                 360                 365
```

-continued

```
atc ctc gat ggc ggt ttt gca agg aag taataccccc actttgaaaa         1393
Ile Leu Asp Gly Gly Phe Ala Arg Lys
        370                 375 acaccccgta cagttacacc agtacggggt gttttttagt taagcttggg tggtgttttt   1453
tagttaagct tgggtg                                                   1469
```

<210> SEQ ID NO 4
<211> LENGTH: 376
<212> TYPE: PRT
<213> ORGANISM: C. glutamicum ATCC 14 752

<400> SEQUENCE: 4

```
Met Thr Asp Phe Pro Thr Leu Pro Ser Glu Phe Ile Pro Gly Asp Gly
 1               5                  10                  15

Arg Phe Gly Cys Gly Pro Ser Lys Val Arg Pro Glu Gln Ile Gln Ala
            20                  25                  30

Ile Val Asp Gly Ser Ala Ser Val Ile Gly Thr Ser His Arg Gln Pro
        35                  40                  45

Ala Val Lys Asn Val Val Gly Ser Ile Arg Glu Gly Leu Ser Asp Leu
    50                  55                  60

Phe Ser Leu Pro Glu Gly Tyr Glu Ile Ile Leu Ser Leu Gly Gly Ala
65                  70                  75                  80

Thr Ala Phe Trp Asp Ala Ala Thr Phe Gly Leu Ile Glu Lys Lys Ser
                85                  90                  95

Gly His Leu Ser Phe Gly Glu Phe Ser Ser Lys Phe Ala Lys Ala Ser
            100                 105                 110

Lys Leu Ala Pro Trp Leu Asp Glu Pro Glu Ile Val Thr Ala Glu Thr
        115                 120                 125

Gly Asp Ser Pro Ala Pro Gln Ala Phe Glu Gly Ala Asp Val Ile Ala
    130                 135                 140

Trp Ala His Asn Glu Thr Ser Thr Gly Ala Met Val Pro Val Leu Arg
145                 150                 155                 160

Pro Glu Gly Ser Glu Gly Ser Leu Val Ala Ile Asp Ala Thr Ser Gly
                165                 170                 175

Ala Gly Gly Leu Pro Val Asp Ile Lys Asn Ser Asp Val Tyr Tyr Phe
            180                 185                 190

Ser Pro Gln Lys Cys Phe Ala Ser Asp Gly Gly Leu Trp Leu Ala Ala
        195                 200                 205

Met Ser Pro Ala Ala Leu Glu Arg Ile Glu Lys Ile Asn Ala Ser Asp
    210                 215                 220

Arg Phe Ile Pro Glu Phe Leu Asn Leu Gln Thr Ala Val Asp Asn Ser
225                 230                 235                 240

Leu Lys Asn Gln Thr Tyr Asn Thr Pro Ala Val Ala Thr Leu Leu Met
                245                 250                 255

Leu Asp Asn Gln Val Lys Trp Met Asn Ser Asn Gly Gly Leu Asp Gly
            260                 265                 270

Met Val Ala Arg Thr Thr Ala Ser Ser Ser Ala Leu Tyr Asn Trp Ala
        275                 280                 285

Glu Ala Arg Glu Glu Ala Ser Pro Tyr Val Ala Asp Ala Ala Lys Arg
    290                 295                 300

Ser Leu Val Val Gly Thr Ile Asp Phe Asp Asp Ser Ile Asp Ala Ala
305                 310                 315                 320

Val Ile Ala Lys Ile Leu Arg Ala Asn Gly Ile Leu Asp Thr Glu Pro
                325                 330                 335
```

```
Tyr Arg Lys Leu Gly Arg Asn Gln Leu Arg Ile Gly Met Phe Pro Ala
        340                 345                 350
Ile Asp Ser Thr Asp Val Glu Lys Leu Thr Gly Ala Ile Asp Phe Ile
            355                 360                 365
Leu Asp Gly Gly Phe Ala Arg Lys
    370                 375

<210> SEQ ID NO 5
<211> LENGTH: 1627
<212> TYPE: DNA
<213> ORGANISM: C. glutanicum ATCC 13 032
<220> FEATURE:
<221> NAME/KEY: CDS
<222> LOCATION: (382)..(1590)
<223> OTHER INFORMATION: ser B  (Phosphoserin-phosphatase)

<400> SEQUENCE: 5
gcagaggcac acactggaca tcacgatgat attaatgctc cagaattggg taccgcccca      60
gcccttgcat ctgactccag ccgctaaaag cgtctgattt aagtcggtac ctgactaaat     120
aagcaccagc cccagcagag ataatctgcc ggggctggtg cttttcatat tccgacttgg     180 ggcaccctg aatacatctc acccaattcc cataactag acaattgccc agcaacgact      240
gataagtctc caatgtcgtg ttccgcgctc agacatgaga caattgttgc cgtgactgaa     300
ctcatccaga atgaatccca agaaatcgct gagctggaag ccggccagca ggttgcattg     360
cgtgaaggtt atcttcctgc g gtg atc aca gtg agc ggt aaa gac cgc cca       411
                        Met Ile Thr Val Ser Gly Lys Asp Arg Pro
                          1               5                  10 ggt gtg act gcc gcg ttc ttt agg gtc ttg tcc gct aat cag gtt cag       459
Gly Val Thr Ala Ala Phe Phe Arg Val Leu Ser Ala Asn Gln Val Gln
                15                  20                  25 gtc ttg gac gtt gag cag tca atg ttc cgt ggc ttt ttg aac ttg gcg       507
Val Leu Asp Val Glu Gln Ser Met Phe Arg Gly Phe Leu Asn Leu Ala
            30                  35                  40 gcg ttt gtg ggt atc gca cct gag cgt gtc gag acc gtc acc aca ggc       555
Ala Phe Val Gly Ile Ala Pro Glu Arg Val Glu Thr Val Thr Thr Gly
    45                  50                  55 ctg act gac acc ctc aag gtg cat gga cag tcc gtg gtg gtg gag ctg       603
Leu Thr Asp Thr Leu Lys Val His Gly Gln Ser Val Val Val Glu Leu
60                  65                  70 cag gaa act gtg cag tcg tcc cgt cct cgt tct tcc cat gtt gtt gtg       651
Gln Glu Thr Val Gln Ser Ser Arg Pro Arg Ser Ser His Val Val Val
 75                  80                  85                  90 gtg ttg ggt gat ccg gtt gat gcg ttg gat att tcc cgc att ggt cag       699
Val Leu Gly Asp Pro Val Asp Ala Leu Asp Ile Ser Arg Ile Gly Gln
                95                 100                 105 acc ctg gcg gat tac gat gcc aac att gac acc att cgt ggc att tcg       747
Thr Leu Ala Asp Tyr Asp Ala Asn Ile Asp Thr Ile Arg Gly Ile Ser
            110                 115                 120 gat tac cct gtg acc ggc ctg gag ctg aag gtg act gtg ccg gat gtc       795
Asp Tyr Pro Val Thr Gly Leu Glu Leu Lys Val Thr Val Pro Asp Val
        125                 130                 135 agc cct ggt ggt ggt gaa gcg atg cgt aag gcg ctt gct gct ctt acc       843
Ser Pro Gly Gly Gly Glu Ala Met Arg Lys Ala Leu Ala Ala Leu Thr
    140                 145                 150 tct gag ctg aat gtg gat att gcg att gag cgt tct ggt ttg ctg cgt       891
Ser Glu Leu Asn Val Asp Ile Ala Ile Glu Arg Ser Gly Leu Leu Arg
155                 160                 165                 170 cgt tct aag cgt ctg gtg tgc ttc gat tgt gat tcc acg ttg atc act       939
```

-continued

```
                Arg Ser Lys Arg Leu Val Cys Phe Asp Cys Asp Ser Thr Leu Ile Thr
                            175                 180                 185 ggt gag gtc att gag atg ctg gcg gct cac gcg ggc aag gaa gct gaa            987
Gly Glu Val Ile Glu Met Leu Ala Ala His Ala Gly Lys Glu Ala Glu
            190                 195                 200 gtt gcg gca gtt act gag cgt gcg atg cgc ggt gag ctc gat ttc gag           1035
Val Ala Ala Val Thr Glu Arg Ala Met Arg Gly Glu Leu Asp Phe Glu
        205                 210                 215 gag tct ctg cgt gag cgt gtg aag gcg ttg gct ggt ttg gat gcg tcg           1083
Glu Ser Leu Arg Glu Arg Val Lys Ala Leu Ala Gly Leu Asp Ala Ser
        220                 225                 230 gtg atc gat gag gtc gct gcc gct att gag ctg acc cct ggt gcg cgc           1131
Val Ile Asp Glu Val Ala Ala Ala Ile Glu Leu Thr Pro Gly Ala Arg
235                 240                 245                 250 acc acg atc cgt acg ctg aac cgc atg ggt tac cag acc gct gtt gtt           1179
Thr Thr Ile Arg Thr Leu Asn Arg Met Gly Tyr Gln Thr Ala Val Val
            255                 260                 265 tcc ggt ggt ttc atc cag gtg ttg gaa ggt ttg gct gag gag ttg gag           1227
Ser Gly Gly Phe Ile Gln Val Leu Glu Gly Leu Ala Glu Glu Leu Glu
        270                 275                 280 ttg gat tat gtc cgc gcc aac act ttg gaa atc gtt gat ggc aag ctg           1275
Leu Asp Tyr Val Arg Ala Asn Thr Leu Glu Ile Val Asp Gly Lys Leu
        285                 290                 295 acc ggc aac gtc acc gga aag atc gtt gac cgc gct gcg aag gct gag           1323
Thr Gly Asn Val Thr Gly Lys Ile Val Asp Arg Ala Ala Lys Ala Glu
        300                 305                 310 ttc ctc cgt gag ttc gct gcg gat tct ggc ctg aag atg tac cag act           1371
Phe Leu Arg Glu Phe Ala Ala Asp Ser Gly Leu Lys Met Tyr Gln Thr
315                 320                 325                 330 gtc gct gtc ggt gat ggc gct aat gac atc gat atg ctc tcc gct gcg           1419
Val Ala Val Gly Asp Gly Ala Asn Asp Ile Asp Met Leu Ser Ala Ala
            335                 340                 345 ggt ctg ggt gtt gct ttc aac gcg aag cct gcg ctg aag gag att gcg           1467
Gly Leu Gly Val Ala Phe Asn Ala Lys Pro Ala Leu Lys Glu Ile Ala
        350                 355                 360 gat act tcc gtg aac cac cca ttc ctc gac gag gtt ttg cac atc atg           1515
Asp Thr Ser Val Asn His Pro Phe Leu Asp Glu Val Leu His Ile Met
        365                 370                 375 ggc att tcc cgc gac gag atc gat ctg gcg gat cag gaa gac ggc act           1563
Gly Ile Ser Arg Asp Glu Ile Asp Leu Ala Asp Gln Glu Asp Gly Thr
        380                 385                 390 ttc cac cgc gtt cca ttg acc aat gcc taaagattcg cttctcgacg                 1610
Phe His Arg Val Pro Leu Thr Asn Ala
395                 400 cccacctcct cctcaag                                                        1627

<210> SEQ ID NO 6
<211> LENGTH: 403
<212> TYPE: PRT
<213> ORGANISM: C. glutanicum ATCC 13 032

<400> SEQUENCE: 6

Met Ile Thr Val Ser Gly Lys Asp Arg Pro Gly Val Thr Ala Ala Phe
  1               5                  10                  15

Phe Arg Val Leu Ser Ala Asn Gln Val Gln Val Leu Asp Val Glu Gln
              20                  25                  30

Ser Met Phe Arg Gly Phe Leu Asn Leu Ala Ala Phe Val Gly Ile Ala
          35                  40                  45

Pro Glu Arg Val Glu Thr Val Thr Thr Gly Leu Thr Asp Thr Leu Lys
```

```
                50                    55                    60
Val His Gly Gln Ser Val Val Glu Leu Gln Glu Thr Val Gln Ser
 65                      70                      75              80

Ser Arg Pro Arg Ser His Val Val Val Leu Gly Asp Pro Val
                 85                      90                  95

Asp Ala Leu Asp Ile Ser Arg Ile Gly Gln Thr Leu Ala Asp Tyr Asp
                100                     105                 110

Ala Asn Ile Asp Thr Ile Arg Gly Ile Ser Asp Tyr Pro Val Thr Gly
            115                     120                 125

Leu Glu Leu Lys Val Thr Val Pro Asp Val Ser Pro Gly Gly Glu
130                     135                     140

Ala Met Arg Lys Ala Leu Ala Ala Leu Thr Ser Glu Leu Asn Val Asp
145                     150                     155             160

Ile Ala Ile Glu Arg Ser Gly Leu Leu Arg Arg Ser Lys Arg Leu Val
                165                     170                 175

Cys Phe Asp Cys Asp Ser Thr Leu Ile Thr Gly Glu Val Ile Glu Met
                180                     185                 190

Leu Ala Ala His Ala Gly Lys Glu Ala Glu Val Ala Ala Val Thr Glu
                195                     200                 205

Arg Ala Met Arg Gly Glu Leu Asp Phe Glu Glu Ser Leu Arg Glu Arg
210                     215                     220

Val Lys Ala Leu Ala Gly Leu Asp Ala Ser Val Ile Asp Glu Val Ala
225                     230                     235             240

Ala Ala Ile Glu Leu Thr Pro Gly Ala Arg Thr Thr Ile Arg Thr Leu
                245                     250                 255

Asn Arg Met Gly Tyr Gln Thr Ala Val Val Ser Gly Gly Phe Ile Gln
                260                     265                 270

Val Leu Glu Gly Leu Ala Glu Glu Leu Glu Leu Asp Tyr Val Arg Ala
            275                     280                 285

Asn Thr Leu Glu Ile Val Asp Gly Lys Leu Thr Gly Asn Val Thr Gly
            290                     295                 300

Lys Ile Val Asp Arg Ala Ala Lys Ala Glu Phe Leu Arg Glu Phe Ala
305                     310                     315             320

Ala Asp Ser Gly Leu Lys Met Tyr Gln Thr Val Ala Val Gly Asp Gly
                325                     330                 335

Ala Asn Asp Ile Asp Met Leu Ser Ala Ala Gly Leu Gly Val Ala Phe
                340                     345                 350

Asn Ala Lys Pro Ala Leu Lys Glu Ile Ala Asp Thr Ser Val Asn His
                355                     360                 365

Pro Phe Leu Asp Glu Val Leu His Ile Met Gly Ile Ser Arg Asp Glu
370                     375                     380

Ile Asp Leu Ala Asp Gln Glu Asp Gly Thr Phe His Arg Val Pro Leu
385                     390                     395             400

Thr Asn Ala

<210> SEQ ID NO 7
<211> LENGTH: 1304
<212> TYPE: DNA
<213> ORGANISM: C. glutanicum ATCC 13 032
<220> FEATURE:
<221> NAME/KEY: CDS
<222> LOCATION: (131)..(1258)
<223> OTHER INFORMATION: ser C (Phosphoserin-phosphatase)

<400> SEQUENCE: 7
```

-continued

```
catcgtttgg gagactgcgt gaagaatcta gggtgctagg aactgacagc ttcagggtta      60
tagttgttgg gtcagatcgt taacgatccc tggccctttt acttccaagc gcagaaagtt     120
gcccgaagac atg acc gac ttc ccc acc ctg ccc tct gag ttc atc cct        169
            Met Thr Asp Phe Pro Thr Leu Pro Ser Glu Phe Ile Pro
              1               5                  10 ggc gac ggc cgt ttc ggc tgc gga cct tcc aag gtt cga cca gaa cag       217
Gly Asp Gly Arg Phe Gly Cys Gly Pro Ser Lys Val Arg Pro Glu Gln
 15              20                  25 att cag gct att gtc gac gga tcc gca tcc gtc atc ggt acc tca cac       265
Ile Gln Ala Ile Val Asp Gly Ser Ala Ser Val Ile Gly Thr Ser His
 30              35                  40                  45 cgt cag ccg gca gta aaa aac gtc gtg ggt tca atc cgc gag gga ctc       313
Arg Gln Pro Ala Val Lys Asn Val Val Gly Ser Ile Arg Glu Gly Leu
                 50                  55                  60 tcc gac ctc ttc tcc ctt cca gaa ggc tac gag atc atc ctt tcc cta       361
Ser Asp Leu Phe Ser Leu Pro Glu Gly Tyr Glu Ile Ile Leu Ser Leu
                 65                  70                  75 ggt ggt gcg acc gca ttc tgg gat gca gca acc ttc gga ctc att gaa       409
Gly Gly Ala Thr Ala Phe Trp Asp Ala Ala Thr Phe Gly Leu Ile Glu
 80              85                  90 aag aag tcc ggt cac ctt tct ttc ggt gag ttc tcc tcc aag ttc gca       457
Lys Lys Ser Gly His Leu Ser Phe Gly Glu Phe Ser Ser Lys Phe Ala
 95              100                 105 aag gct tct aag ctt gct cct tgg ctc gac gag cca gag atc gtc acc       505
Lys Ala Ser Lys Leu Ala Pro Trp Leu Asp Glu Pro Glu Ile Val Thr
110             115                 120                 125 gca gaa acc ggt gac tct ccg gcc cca cag gca ttc gaa ggc gcc gat       553
Ala Glu Thr Gly Asp Ser Pro Ala Pro Gln Ala Phe Glu Gly Ala Asp
                130                 135                 140 gtt att gca tgg gca cac aac gaa acc tcc gct ggc gcc atg gtt cca       601
Val Ile Ala Trp Ala His Asn Glu Thr Ser Ala Gly Ala Met Val Pro
                145                 150                 155 gtt ctt cgc ccc gaa ggc tct gaa ggc tcc ctg gtt gcc att gac gca       649
Val Leu Arg Pro Glu Gly Ser Glu Gly Ser Leu Val Ala Ile Asp Ala
                160                 165                 170 acc tcc ggc gct ggt gga ctg cca gta gac atc aag aac tcc gat gtt       697
Thr Ser Gly Ala Gly Gly Leu Pro Val Asp Ile Lys Asn Ser Asp Val
175                 180                 185 tac tac ttc tcc cca cag aag tgc ttc gca tcc gac ggt ggc ctg tgg       745
Tyr Tyr Phe Ser Pro Gln Lys Cys Phe Ala Ser Asp Gly Gly Leu Trp
190                 195                 200                 205 ctt gca gcg atg agc cca gca gct ctc gag cgc atc gag aag atc aac       793
Leu Ala Ala Met Ser Pro Ala Ala Leu Glu Arg Ile Glu Lys Ile Asn
                210                 215                 220 gct tcc gat cgc ttc atc cct gag ttc ctc aac ctg cag acc gca gtg       841
Ala Ser Asp Arg Phe Ile Pro Glu Phe Leu Asn Leu Gln Thr Ala Val
                225                 230                 235 gat aac tcc ctg aag aac cag acc tac aac acc cca gct gtt gct acc       889
Asp Asn Ser Leu Lys Asn Gln Thr Tyr Asn Thr Pro Ala Val Ala Thr
                240                 245                 250 ttg ctg atg ctg gac aac cag gtc aag tgg atg aac tcc aac ggc ggc       937
Leu Leu Met Leu Asp Asn Gln Val Lys Trp Met Asn Ser Asn Gly Gly
255                 260                 265 ctg gat gga atg gtt gct cgc acc aca gca agc tcc tcc gcc ctg tac       985
Leu Asp Gly Met Val Ala Arg Thr Thr Ala Ser Ser Ser Ala Leu Tyr
270                 275                 280                 285 aac tgg gct gag gct cgc gag gag gca tcc cca tac gtg gca gat gca      1033
Asn Trp Ala Glu Ala Arg Glu Glu Ala Ser Pro Tyr Val Ala Asp Ala
                290                 295                 300
```

```
gct aag cgc tcc ctc gtt gtc ggc acc atc gac ttc gat gac tcc atc   1081
Ala Lys Arg Ser Leu Val Val Gly Thr Ile Asp Phe Asp Asp Ser Ile
        305                 310                 315 gac gca gca gtg atc gct aag ata ctg cgc gca aac ggc atc ctg gac   1129
Asp Ala Ala Val Ile Ala Lys Ile Leu Arg Ala Asn Gly Ile Leu Asp
320                 325                 330 acc gag cct tac cgc aag ctg gga cgc aac cag ctg cgc atc ggt atg   1177
Thr Glu Pro Tyr Arg Lys Leu Gly Arg Asn Gln Leu Arg Ile Gly Met
            335                 340                 345 ttc cca gcg atc gat tcc acc gat gtg gaa aag ctc acc gga gca atc   1225
Phe Pro Ala Ile Asp Ser Thr Asp Val Glu Lys Leu Thr Gly Ala Ile
350                 355                 360                 365 gac ttc atc ctc gat ggc ggt ttt gca agg aag taatacccccc actttgaaaa 1278
Asp Phe Ile Leu Asp Gly Gly Phe Ala Arg Lys
                370                 375 acaccccgta cagttacacc agtacg                                      1304

<210> SEQ ID NO 8
<211> LENGTH: 376
<212> TYPE: PRT
<213> ORGANISM: C. glutanicum ATCC 13 032

<400> SEQUENCE: 8

Met Thr Asp Phe Pro Thr Leu Pro Ser Glu Phe Ile Pro Gly Asp Gly
 1               5                  10                  15

Arg Phe Gly Cys Gly Pro Ser Lys Val Arg Pro Glu Gln Ile Gln Ala
            20                  25                  30

Ile Val Asp Gly Ser Ala Ser Val Ile Gly Thr Ser His Arg Gln Pro
        35                  40                  45

Ala Val Lys Asn Val Val Gly Ser Ile Arg Glu Gly Leu Ser Asp Leu
    50                  55                  60

Phe Ser Leu Pro Glu Gly Tyr Glu Ile Ile Leu Ser Leu Gly Gly Ala
65                  70                  75                  80

Thr Ala Phe Trp Asp Ala Ala Thr Phe Gly Leu Ile Glu Lys Lys Ser
                85                  90                  95

Gly His Leu Ser Phe Gly Glu Phe Ser Ser Lys Phe Ala Lys Ala Ser
            100                 105                 110

Lys Leu Ala Pro Trp Leu Asp Glu Pro Glu Ile Val Thr Ala Glu Thr
        115                 120                 125

Gly Asp Ser Pro Ala Pro Gln Ala Phe Glu Gly Ala Asp Val Ile Ala
    130                 135                 140

Trp Ala His Asn Glu Thr Ser Ala Gly Ala Met Val Pro Val Leu Arg
145                 150                 155                 160

Pro Glu Gly Ser Glu Gly Ser Leu Val Ala Ile Asp Ala Thr Ser Gly
                165                 170                 175

Ala Gly Gly Leu Pro Val Asp Ile Lys Asn Ser Asp Val Tyr Tyr Phe
            180                 185                 190

Ser Pro Gln Lys Cys Phe Ala Ser Asp Gly Gly Leu Trp Leu Ala Ala
        195                 200                 205

Met Ser Pro Ala Ala Leu Glu Arg Ile Glu Lys Ile Asn Ala Ser Asp
    210                 215                 220

Arg Phe Ile Pro Glu Phe Leu Asn Leu Gln Thr Ala Val Asp Asn Ser
225                 230                 235                 240

Leu Lys Asn Gln Thr Tyr Asn Thr Pro Ala Val Ala Thr Leu Leu Met
                245                 250                 255
```

-continued

```
Leu Asp Asn Gln Val Lys Trp Met Asn Ser Asn Gly Gly Leu Asp Gly
            260                 265                 270
Met Val Ala Arg Thr Thr Ala Ser Ser Ala Leu Tyr Asn Trp Ala
        275                 280                 285
Glu Ala Arg Glu Ala Ser Pro Tyr Val Ala Asp Ala Ala Lys Arg
        290                 295                 300
Ser Leu Val Val Gly Thr Ile Asp Phe Asp Ser Ile Asp Ala Ala
305                 310                 315                 320
Val Ile Ala Lys Ile Leu Arg Ala Asn Gly Ile Leu Asp Thr Glu Pro
                325                 330                 335
Tyr Arg Lys Leu Gly Arg Asn Gln Leu Arg Ile Gly Met Phe Pro Ala
                340                 345                 350
Ile Asp Ser Thr Asp Val Glu Lys Leu Thr Gly Ala Ile Asp Phe Ile
                355                 360                 365
Leu Asp Gly Gly Phe Ala Arg Lys
        370                 375
```

<210> SEQ ID NO 9
<211> LENGTH: 2817
<212> TYPE: DNA
<213> ORGANISM: C. glutamicum ATCC 14 752
<220> FEATURE:
<221> NAME/KEY: CDS
<222> LOCATION: (398)..(1867)
<223> OTHER INFORMATION: thr E  (Threonin-exportcarrier)

<400> SEQUENCE: 9

```
aatgaaataa tccccctcacc aactggcgac attcaaacac cgtttcattt ccaaacatcg      60
agccaaggga aaagaaagcc cctaagcccc gtgttattaa atggagactc tttggagacc     120
tcaagccaaa aagggggcatt ttcattaaga aatacccct ttgacctggt gttattgagc     180
tggagaagag acttgaactc tcaacctacg cattacaagt gcgttgcgct gccaattgcg     240
ccactccagc accgcagatg ctgatgatca acaactacga atacgtatct tagcgtatgt     300
gtacatcaca atggaattcg gggctagagt atctggtgaa ccgtgcataa acgacctgtg     360
attggactct ttttccttgc aaaatgtttt ccagcgg atg ttg agt ttt gcg acc     415
                                         Met Leu Ser Phe Ala Thr
                                          1               5 ctt cgt ggc cgc att tca aca gtt gac gct gca aaa gcc gca cct ccg      463
Leu Arg Gly Arg Ile Ser Thr Val Asp Ala Ala Lys Ala Ala Pro Pro
             10                  15                  20 cca tcg cca cta gcc ccg att gat ctc act gac cat agt caa gtg gcc      511
Pro Ser Pro Leu Ala Pro Ile Asp Leu Thr Asp His Ser Gln Val Ala
         25                  30                  35 ggt gtg atg aat ttg gct gcg aga att ggc gat att ttg ctt tct tca      559
Gly Val Met Asn Leu Ala Ala Arg Ile Gly Asp Ile Leu Leu Ser Ser
     40                  45                  50 ggt acg tca aac agt gat acc aag gtg caa gtt cga gcg gtg acc tct      607
Gly Thr Ser Asn Ser Asp Thr Lys Val Gln Val Arg Ala Val Thr Ser
 55                  60                  65                  70 gcg tat ggc ctg tac tat acg cat gtg gat atc acg ttg aat acg atc      655
Ala Tyr Gly Leu Tyr Tyr Thr His Val Asp Ile Thr Leu Asn Thr Ile
                 75                  80                  85 acc atc ttc acc aac atc ggt gtg gag agg aag atg ccg gtc aac gtg      703
Thr Ile Phe Thr Asn Ile Gly Val Glu Arg Lys Met Pro Val Asn Val
             90                  95                 100 ttt cat gtt gtg ggc aag ttg gac acc aac ttc tcc aaa ctg tct gag      751
Phe His Val Val Gly Lys Leu Asp Thr Asn Phe Ser Lys Leu Ser Glu
        105                 110                 115
```

-continued

| | |
|---|---|
| gtt gac cgt ttg atc cgt tcc att cag gct ggt gct acc ccg cct gag<br>Val Asp Arg Leu Ile Arg Ser Ile Gln Ala Gly Ala Thr Pro Pro Glu<br>120                   125                   130 | 799 |
| gtt gcc gag aaa att ctg gac gag ttg gag caa tcg cct gcg tct tat<br>Val Ala Glu Lys Ile Leu Asp Glu Leu Glu Gln Ser Pro Ala Ser Tyr<br>135                   140                   145                   150 | 847 |
| ggt ttc cct gtt gcg ttg ctt ggc tgg gca atg atg ggt ggc gct gtt<br>Gly Phe Pro Val Ala Leu Leu Gly Trp Ala Met Met Gly Gly Ala Val<br>                  155                   160                   165 | 895 |
| gct gtg ctg ttg ggt ggt gga tgg cag gtt tcc cta att gct ttt att<br>Ala Val Leu Leu Gly Gly Gly Trp Gln Val Ser Leu Ile Ala Phe Ile<br>                  170                   175                   180 | 943 |
| acc gcg ttc acg atc att gcc acg acg tca ttt ttg gga aag aag ggt<br>Thr Ala Phe Thr Ile Ile Ala Thr Thr Ser Phe Leu Gly Lys Lys Gly<br>185                   190                   195 | 991 |
| ttg cct act ttc ttc caa aat gtt gtt ggt ggt ttt att gcc acg ctg<br>Leu Pro Thr Phe Phe Gln Asn Val Val Gly Gly Phe Ile Ala Thr Leu<br>200                   205                   210 | 1039 |
| cct gca tcg att gct tat tct ttg gcg ttg caa ttt ggt ctt gag atc<br>Pro Ala Ser Ile Ala Tyr Ser Leu Ala Leu Gln Phe Gly Leu Glu Ile<br>215                   220                   225                   230 | 1087 |
| aaa ccg agc cag atc atc gca tct gga att gtt gtg ctg ttg gca ggt<br>Lys Pro Ser Gln Ile Ile Ala Ser Gly Ile Val Val Leu Leu Ala Gly<br>                  235                   240                   245 | 1135 |
| ttg aca ctt gtg caa tct ctg cag gac ggc atc acg ggc gct ccg gtg<br>Leu Thr Leu Val Gln Ser Leu Gln Asp Gly Ile Thr Gly Ala Pro Val<br>                250                   255                   260 | 1183 |
| aca gca agt gca cga ttt ttt gaa aca ctc ctg ttt acc ggc ggc att<br>Thr Ala Ser Ala Arg Phe Phe Glu Thr Leu Leu Phe Thr Gly Gly Ile<br>265                   270                   275 | 1231 |
| gtt gct ggc gtg ggt ttg ggc att cag ctt tct gaa atc ttg cat gtc<br>Val Ala Gly Val Gly Leu Gly Ile Gln Leu Ser Glu Ile Leu His Val<br>280                   285                   290 | 1279 |
| atg ttg cct gcc atg gag tcc gct gca gca cct aat tat tcg tct aca<br>Met Leu Pro Ala Met Glu Ser Ala Ala Ala Pro Asn Tyr Ser Ser Thr<br>295                   300                   305                   310 | 1327 |
| ttc gcc cgc att atc gct ggt ggc gtc acc gca gcg gcc ttc gca gtg<br>Phe Ala Arg Ile Ile Ala Gly Gly Val Thr Ala Ala Ala Phe Ala Val<br>                  315                   320                   325 | 1375 |
| ggt tgt tac gcg gag tgg tcc tcg gtg att att gcg ggg ctt act gcg<br>Gly Cys Tyr Ala Glu Trp Ser Ser Val Ile Ile Ala Gly Leu Thr Ala<br>                  330                   335                   340 | 1423 |
| ctg atg ggt tct gcg ttt tat tac ctc ttc gtt gtt tat tta ggc ccc<br>Leu Met Gly Ser Ala Phe Tyr Tyr Leu Phe Val Val Tyr Leu Gly Pro<br>                  345                   350                   355 | 1471 |
| gtc tct gcc gct gcg att gct gca aca gca gtt ggt ttc act ggt ggt<br>Val Ser Ala Ala Ala Ile Ala Ala Thr Ala Val Gly Phe Thr Gly Gly<br>360                   365                   370 | 1519 |
| ttg ctt gcc cgt cga ttc ttg att cca ccg ttg att gtg gcg att gcc<br>Leu Leu Ala Arg Arg Phe Leu Ile Pro Pro Leu Ile Val Ala Ile Ala<br>375                   380                   385                   390 | 1567 |
| ggc atc aca cca atg ctt cca ggt cta gca att tac cgc gga atg tac<br>Gly Ile Thr Pro Met Leu Pro Gly Leu Ala Ile Tyr Arg Gly Met Tyr<br>                  395                   400                   405 | 1615 |
| gcc acc ttg aat gat caa aca ctc atg ggt ttc acc aac att gcg gtt<br>Ala Thr Leu Asn Asp Gln Thr Leu Met Gly Phe Thr Asn Ile Ala Val<br>                  410                   415                   420 | 1663 |
| gct tta gcc act gct tca tca ctt gcc gct ggc gtg gtt ttg ggt gag<br>Ala Leu Ala Thr Ala Ser Ser Leu Ala Ala Gly Val Val Leu Gly Glu | 1711 |

-continued

```
                425                 430                 435
tgg att gcc cgc agg cta cgt cgt cca cca cgc ttc aac cca tac cgt    1759
Trp Ile Ala Arg Arg Leu Arg Arg Pro Pro Arg Phe Asn Pro Tyr Arg
    440                 445                 450 gca ttt acc aag gcg aat gag ttc tcc ttc cag gag gaa gct gag cag    1807
Ala Phe Thr Lys Ala Asn Glu Phe Ser Phe Gln Glu Glu Ala Glu Gln
455                 460                 465                 470 aat cag cgc cgg cag aga aaa cgt cca aag act aat caa aga ttc ggt    1855
Asn Gln Arg Arg Gln Arg Lys Arg Pro Lys Thr Asn Gln Arg Phe Gly
                475                 480                 485 aat aaa agg taa aaatcaacct gcttaggcgt ctttcgctta aatagcgtag        1907
Asn Lys Arg
        490 aatatcgggt cgatcgcttt taaacactca ggaggatcct tgccggccaa atcacggac   1967 actcgtccca ccccagaatc ccttcacgct gttgaagagg aaaccgcagc cggtgcccgc  2027 aggattgttg ccacctattc taaggacttc ttcgacggcg tcactttgat gtgcatgctc  2087 ggcgttgaac ctcagggcct gcgttacacc aaggtcgctt ctgaacacga ggaagctcag  2147 ccaaagaagg ctacaaagcg gactcgtaag gcaccagcta agaaggctgc tgctaagaaa  2207 acgaccaaga agaccactaa gaaaactact aaaaagacca ccgcaaagaa gaccacaaag  2267 aagtcttaag ccggatctta tatggatgat tccaatagct ttgtagttgt tgctaaccgt  2327 ctgccagtgg atatgactgt ccacccagat ggtagctata gcatctcccc cagccccggt  2387 ggccttgtca cggggctttc ccccgttctg aacaacatc gtggatgttg ggtcggatgg   2447 cctggaactg tagatgttgc acccgaacca tttcgaacag atacgggtgt tttgctgcac  2507 cctgttgtcc tcactgcaag tgactatgaa ggcttctacg agggcttttc aaacgcaacg  2567 ctgtggcctc ttttccacga tttgattgtt actccggtgt acaacaccga ttggtggcat  2627 gcgtttcggg aagtaaacct caagttcgct gaagccgtga gccaagtggc ggcacacggt  2687 gccactgtgt gggtgcagga ctatcagctg ttgctggttc ctggcatttt gcgccagatg  2747 cgccctgatt tgaagatcgg tttcttcctc cacattccct tcccttcccc tgatctgttc  2807 cgtcagctgc                                                         2817
```

<210> SEQ ID NO 10
<211> LENGTH: 489
<212> TYPE: PRT
<213> ORGANISM: C. glutamicum ATCC 14 752

<400> SEQUENCE: 10

```
Met Leu Ser Phe Ala Thr Leu Arg Gly Arg Ile Ser Thr Val Asp Ala
1               5                   10                  15

Ala Lys Ala Ala Pro Pro Ser Pro Leu Ala Pro Ile Asp Leu Thr
            20                  25                  30

Asp His Ser Gln Val Ala Gly Val Met Asn Leu Ala Ala Arg Ile Gly
        35                  40                  45

Asp Ile Leu Leu Ser Ser Gly Thr Ser Asn Ser Asp Thr Lys Val Gln
    50                  55                  60

Val Arg Ala Val Thr Ser Ala Tyr Gly Leu Tyr Tyr Thr His Val Asp
65                  70                  75                  80

Ile Thr Leu Asn Thr Ile Thr Ile Phe Thr Asn Ile Gly Val Glu Arg
                85                  90                  95

Lys Met Pro Val Asn Val Phe His Val Val Gly Lys Leu Asp Thr Asn
            100                 105                 110
```

Phe Ser Lys Leu Ser Glu Val Asp Arg Leu Ile Arg Ser Ile Gln Ala
            115                 120                 125

Gly Ala Thr Pro Pro Glu Val Ala Glu Lys Ile Leu Asp Glu Leu Glu
        130                 135                 140

Gln Ser Pro Ala Ser Tyr Gly Phe Pro Val Ala Leu Leu Gly Trp Ala
145                 150                 155                 160

Met Met Gly Gly Ala Val Ala Val Leu Leu Gly Gly Trp Gln Val
                165                 170                 175

Ser Leu Ile Ala Phe Ile Thr Ala Phe Thr Ile Ile Ala Thr Thr Ser
            180                 185                 190

Phe Leu Gly Lys Lys Gly Leu Pro Thr Phe Phe Gln Asn Val Val Gly
        195                 200                 205

Gly Phe Ile Ala Thr Leu Pro Ala Ser Ile Ala Tyr Ser Leu Ala Leu
210                 215                 220

Gln Phe Gly Leu Glu Ile Lys Pro Ser Gln Ile Ile Ala Ser Gly Ile
225                 230                 235                 240

Val Val Leu Leu Ala Gly Leu Thr Leu Val Gln Ser Leu Gln Asp Gly
            245                 250                 255

Ile Thr Gly Ala Pro Val Thr Ala Ser Ala Arg Phe Phe Glu Thr Leu
        260                 265                 270

Leu Phe Thr Gly Gly Ile Val Ala Gly Val Gly Leu Gly Ile Gln Leu
    275                 280                 285

Ser Glu Ile Leu His Val Met Leu Pro Ala Met Glu Ser Ala Ala Ala
290                 295                 300

Pro Asn Tyr Ser Ser Thr Phe Ala Arg Ile Ile Ala Gly Gly Val Thr
305                 310                 315                 320

Ala Ala Ala Phe Ala Val Gly Cys Tyr Ala Glu Trp Ser Ser Val Ile
            325                 330                 335

Ile Ala Gly Leu Thr Ala Leu Met Gly Ser Ala Phe Tyr Tyr Leu Phe
        340                 345                 350

Val Val Tyr Leu Gly Pro Val Ser Ala Ala Ile Ala Ala Thr Ala
    355                 360                 365

Val Gly Phe Thr Gly Gly Leu Leu Ala Arg Arg Phe Leu Ile Pro Pro
    370                 375                 380

Leu Ile Val Ala Ile Ala Gly Ile Thr Pro Met Leu Pro Gly Leu Ala
385                 390                 395                 400

Ile Tyr Arg Gly Met Tyr Ala Thr Leu Asn Asp Gln Thr Leu Met Gly
            405                 410                 415

Phe Thr Asn Ile Ala Val Ala Leu Ala Thr Ala Ser Ser Leu Ala Ala
        420                 425                 430

Gly Val Val Leu Gly Glu Trp Ile Ala Arg Arg Leu Arg Arg Pro Pro
    435                 440                 445

Arg Phe Asn Pro Tyr Arg Ala Phe Thr Lys Ala Asn Glu Phe Ser Phe
450                 455                 460

Gln Glu Glu Ala Glu Gln Asn Gln Arg Arg Gln Arg Lys Arg Pro Lys
465                 470                 475                 480

Thr Asn Gln Arg Phe Gly Asn Lys Arg
            485

<210> SEQ ID NO 11
<211> LENGTH: 1909
<212> TYPE: DNA
<213> ORGANISM: C. glutanicum ATCC 13 032
<220> FEATURE:
<221> NAME/KEY: CDS -continued
<222> LOCATION: (280)..(1746)
<223> OTHER INFORMATION: thr E  (Threonin-exportcarrier)

<400> SEQUENCE: 11

| | |
|---|---|
| agcttgcatg cctgcaggtc gactctagag gatccccccc ctttgacctg gtgttattga | 60 |
| gctggagaag agacttgaac tctcaaccta cgcattacaa gtgcgttgcg ctgccaattg | 120 |
| cgccactcca gcaccgcaga tgctgatgat caacaactac gaatacgtat cttagcgtat | 180 |
| gtgtacatca caatggaatt cggggctaga gtatctggtg aaccgtgcat aaacgacctg | 240 |
| tgattggact cttttcctt gcaaaatgtt ttccagcgg atg ttg agt ttt gcg | 294 |
|                                                                 Met Leu Ser Phe Ala<br>                                                                1             5 | |
| acc ctt cgt ggc cgc att tca aca gtt gac gct gca aaa gcc gca cct<br>Thr Leu Arg Gly Arg Ile Ser Thr Val Asp Ala Ala Lys Ala Ala Pro<br>                10                    15                   20 | 342 |
| ccg cca tcg cca cta gcc ccg att gat ctc act gac cat agt caa gtg<br>Pro Pro Ser Pro Leu Ala Pro Ile Asp Leu Thr Asp His Ser Gln Val<br>                    25                    30                   35 | 390 |
| gcc ggt gtg atg aat ttg gct gcg aga att ggc gat att ttg ctt tct<br>Ala Gly Val Met Asn Leu Ala Ala Arg Ile Gly Asp Ile Leu Leu Ser<br>          40                    45                    50 | 438 |
| tca ggt acg tca aat agt gac acc aag gta caa gtt cga gca gtg acc<br>Ser Gly Thr Ser Asn Ser Asp Thr Lys Val Gln Val Arg Ala Val Thr<br> 55                    60                    65 | 486 |
| tct gcg tac ggt ttg tac tac acg cac gtg gat atc acg ttg aat acg<br>Ser Ala Tyr Gly Leu Tyr Tyr Thr His Val Asp Ile Thr Leu Asn Thr<br> 70                    75                    80                    85 | 534 |
| atc acc atc ttc acc aac atc ggt gtg gag agg aag atg ccg gtc aac<br>Ile Thr Ile Phe Thr Asn Ile Gly Val Glu Arg Lys Met Pro Val Asn<br>                    90                    95                  100 | 582 |
| gtg ttt cat gtt gta ggc aag ttg gac acc aac ttc tcc aaa ctg tct<br>Val Phe His Val Val Gly Lys Leu Asp Thr Asn Phe Ser Lys Leu Ser<br>          105                   110                   115 | 630 |
| gag gtt gac cgt ttg atc cgt tcc att cag gct ggt gcg acc ccg cct<br>Glu Val Asp Arg Leu Ile Arg Ser Ile Gln Ala Gly Ala Thr Pro Pro<br>          120                   125                   130 | 678 |
| gag gtt gcc gag aaa atc ctg gac gag ttg gag caa tcc cct gcg tct<br>Glu Val Ala Glu Lys Ile Leu Asp Glu Leu Glu Gln Ser Pro Ala Ser<br>135                   140                   145 | 726 |
| tat ggt ttc cct gtt gcg ttg ctt ggc tgg gca atg atg ggt ggt gct<br>Tyr Gly Phe Pro Val Ala Leu Leu Gly Trp Ala Met Met Gly Gly Ala<br>150                   155                   160                   165 | 774 |
| gtt gct gtg ctg ttg ggt ggt gga tgg cag gtt tcc cta att gct ttt<br>Val Ala Val Leu Leu Gly Gly Gly Trp Gln Val Ser Leu Ile Ala Phe<br>          170                   175                   180 | 822 |
| att acc gcg ttc acg atc att gcc acg acg tca ttt ttg gga aag aag<br>Ile Thr Ala Phe Thr Ile Ile Ala Thr Thr Ser Phe Leu Gly Lys Lys<br>          185                   190                   195 | 870 |
| ggt ttg cct act ttc ttc caa aat gtt gtt ggt ggt ttt att gcc acg<br>Gly Leu Pro Thr Phe Phe Gln Asn Val Val Gly Gly Phe Ile Ala Thr<br>          200                   205                   210 | 918 |
| ctg cct gca tcg att gct tat tct ttg gcg ttg caa ttt ggt ctt gag<br>Leu Pro Ala Ser Ile Ala Tyr Ser Leu Ala Leu Gln Phe Gly Leu Glu<br>          215                   220                   225 | 966 |
| atc aaa ccg agc cag atc atc gca tct gga att gtt gtg ctg ttg gca<br>Ile Lys Pro Ser Gln Ile Ile Ala Ser Gly Ile Val Val Leu Leu Ala<br>230                   235                   240                   245 | 1014 |
| ggt ttg aca ctc gtg caa tct ctg cag gac ggc atc acg ggc gct ccg<br>Gly Leu Thr Leu Val Gln Ser Leu Gln Asp Gly Ile Thr Gly Ala Pro | 1062 |

-continued

```
                250                 255                 260
gtg aca gca agt gca cga ttt ttc gaa aca ctc ctg ttt acc ggc ggc       1110
Val Thr Ala Ser Ala Arg Phe Phe Glu Thr Leu Leu Phe Thr Gly Gly
            265                 270                 275 att gtt gct ggc gtg ggt ttg ggc att cag ctt tct gaa atc ttg cat       1158
Ile Val Ala Gly Val Gly Leu Gly Ile Gln Leu Ser Glu Ile Leu His
        280                 285                 290 gtc atg ttg cct gcc atg gag tcc gct gca gca cct aat tat tcg tct       1206
Val Met Leu Pro Ala Met Glu Ser Ala Ala Ala Pro Asn Tyr Ser Ser
295                 300                 305 aca ttc gcc cgc att atc gct ggt ggc gtc acc gca gcg gcc ttc gca       1254
Thr Phe Ala Arg Ile Ile Ala Gly Gly Val Thr Ala Ala Phe Ala
310                 315                 320                 325 gtg ggt tgt tac gcg gag tgg tcc tcg gtg att att gcg ggg ctt act       1302
Val Gly Cys Tyr Ala Glu Trp Ser Ser Val Ile Ile Ala Gly Leu Thr
            330                 335                 340 gcg ctg atg ggt tct gcg ttt tat tac ctc ttc gtt gtt tat tta ggc       1350
Ala Leu Met Gly Ser Ala Phe Tyr Tyr Leu Phe Val Val Tyr Leu Gly
        345                 350                 355 ccc gtc tct gcc gct gcg att gct gca aca gca gtt ggt ttc act ggt       1398
Pro Val Ser Ala Ala Ala Ile Ala Ala Thr Ala Val Gly Phe Thr Gly
            360                 365                 370 ggt ttg ctt gcc cgt cga ttc ttg att cca ccg ttg att gtg gcg att       1446
Gly Leu Leu Ala Arg Arg Phe Leu Ile Pro Pro Leu Ile Val Ala Ile
375                 380                 385 gcc ggc atc aca cca atg ctt cca ggt cta gca att tac cgc gga atg       1494
Ala Gly Ile Thr Pro Met Leu Pro Gly Leu Ala Ile Tyr Arg Gly Met
390                 395                 400                 405 tac gcc acc ctg aat gat caa aca ctc atg ggt ttc acc aac att gcg       1542
Tyr Ala Thr Leu Asn Asp Gln Thr Leu Met Gly Phe Thr Asn Ile Ala
            410                 415                 420 gtt gct tta gcc act gct tca tca ctt gcc gct ggc gtg gtt ttg ggt       1590
Val Ala Leu Ala Thr Ala Ser Ser Leu Ala Ala Gly Val Val Leu Gly
        425                 430                 435 gag tgg att gcc cgc agg cta cgt cgt cca cca cgc ttc aac cca tac       1638
Glu Trp Ile Ala Arg Arg Leu Arg Arg Pro Pro Arg Phe Asn Pro Tyr
            440                 445                 450 cgt gca ttt acc aag gcg aat gag ttc tcc ttc cag gag gaa gct gag       1686
Arg Ala Phe Thr Lys Ala Asn Glu Phe Ser Phe Gln Glu Glu Ala Glu
455                 460                 465 cag aat cag cgc cgg cag aga aaa cgt cca aag act aat cag aga ttc       1734
Gln Asn Gln Arg Arg Gln Arg Lys Arg Pro Lys Thr Asn Gln Arg Phe
470                 475                 480                 485 ggt aat aaa agg taaaaatcaa cctgcttagg cgtctttcgc ttaaatagcg           1786
Gly Asn Lys Arg tagaatatcg ggtcgatcgc ttttaaacac tcaggaggat ccttgccggc caaaatcacg    1846
gacactcgtc ccaccccaga atcccttcac gctgttgaag aggaaaccgc agccggggta    1906
ccg                                                                   1909

<210> SEQ ID NO 12
<211> LENGTH: 489
<212> TYPE: PRT
<213> ORGANISM: C. glutanicum ATCC 13 032

<400> SEQUENCE: 12

Met Leu Ser Phe Ala Thr Leu Arg Gly Arg Ile Ser Thr Val Asp Ala
 1               5                  10                  15

Ala Lys Ala Ala Pro Pro Pro Ser Pro Leu Ala Pro Ile Asp Leu Thr
```

-continued

```
                 20                  25                  30
Asp His Ser Gln Val Ala Gly Val Met Asn Leu Ala Ala Arg Ile Gly
        35                  40                  45

Asp Ile Leu Leu Ser Ser Gly Thr Ser Asn Ser Asp Thr Lys Val Gln
    50                  55                  60

Val Arg Ala Val Thr Ser Ala Tyr Gly Leu Tyr Tyr Thr His Val Asp
65                  70                  75                  80

Ile Thr Leu Asn Thr Ile Thr Ile Phe Thr Asn Ile Gly Val Glu Arg
                85                  90                  95

Lys Met Pro Val Asn Val Phe His Val Val Gly Lys Leu Asp Thr Asn
            100                 105                 110

Phe Ser Lys Leu Ser Glu Val Asp Arg Leu Ile Arg Ser Ile Gln Ala
        115                 120                 125

Gly Ala Thr Pro Pro Glu Val Ala Glu Lys Ile Leu Asp Glu Leu Glu
    130                 135                 140

Gln Ser Pro Ala Ser Tyr Gly Phe Pro Val Ala Leu Leu Gly Trp Ala
145                 150                 155                 160

Met Met Gly Gly Ala Val Ala Val Leu Leu Gly Gly Trp Gln Val
            165                 170                 175

Ser Leu Ile Ala Phe Ile Thr Ala Phe Thr Ile Ile Ala Thr Thr Ser
        180                 185                 190

Phe Leu Gly Lys Lys Gly Leu Pro Thr Phe Gln Asn Val Val Gly
        195                 200                 205

Gly Phe Ile Ala Thr Leu Pro Ala Ser Ile Ala Tyr Ser Leu Ala Leu
    210                 215                 220

Gln Phe Gly Leu Glu Ile Lys Pro Ser Gln Ile Ile Ala Ser Gly Ile
225                 230                 235                 240

Val Val Leu Leu Ala Gly Leu Thr Leu Val Gln Ser Leu Gln Asp Gly
                245                 250                 255

Ile Thr Gly Ala Pro Val Thr Ala Ser Ala Arg Phe Phe Glu Thr Leu
            260                 265                 270

Leu Phe Thr Gly Gly Ile Val Ala Gly Val Gly Leu Gly Ile Gln Leu
        275                 280                 285

Ser Glu Ile Leu His Val Met Leu Pro Ala Met Glu Ser Ala Ala Ala
    290                 295                 300

Pro Asn Tyr Ser Ser Thr Phe Ala Arg Ile Ile Ala Gly Gly Val Thr
305                 310                 315                 320

Ala Ala Ala Phe Ala Val Gly Cys Tyr Ala Glu Trp Ser Ser Val Ile
                325                 330                 335

Ile Ala Gly Leu Thr Ala Leu Met Gly Ser Ala Phe Tyr Tyr Leu Phe
            340                 345                 350

Val Val Tyr Leu Gly Pro Val Ser Ala Ala Ile Ala Ala Thr Ala
        355                 360                 365

Val Gly Phe Thr Gly Gly Leu Leu Ala Arg Arg Phe Leu Ile Pro Pro
    370                 375                 380

Leu Ile Val Ala Ile Ala Gly Ile Thr Pro Met Leu Pro Gly Leu Ala
385                 390                 395                 400

Ile Tyr Arg Gly Met Tyr Ala Thr Leu Asn Asp Gln Thr Leu Met Gly
                405                 410                 415

Phe Thr Asn Ile Ala Val Ala Leu Ala Thr Ala Ser Ser Leu Ala Ala
            420                 425                 430

Gly Val Val Leu Gly Glu Trp Ile Ala Arg Arg Leu Arg Arg Pro Pro
        435                 440                 445
```

```
Arg Phe Asn Pro Tyr Arg Ala Phe Thr Lys Ala Asn Glu Phe Ser Phe
    450             455             460

Gln Glu Glu Ala Glu Gln Asn Gln Arg Arg Gln Arg Lys Arg Pro Lys
465             470             475             480

Thr Asn Gln Arg Phe Gly Asn Lys Arg
                485
```